(12) United States Patent
Suzuki et al.

(10) Patent No.: US 6,491,676 B1
(45) Date of Patent: *Dec. 10, 2002

(54) ABSORBENT ARTICLE AND METHOD OF MANUFACTURE

(75) Inventors: Migaku Suzuki, Kanagawa; Hiroaki Fukui, Saitama, both of (JP)

(73) Assignee: Paragon Trade Brands, Inc., Norcross, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 137 days.

(21) Appl. No.: 08/793,369

(22) Filed: Feb. 24, 1997

(30) Foreign Application Priority Data

Aug. 24, 1994 (JP) ............................................. 94-199599
Aug. 24, 1994 (JP) ............................................. 94-199600
Aug. 24, 1994 (JP) ............................................. 94-199601

(51) Int. Cl.$^7$ ......................... A61F 13/15; A61F 13/20; A41B 9/00; B32B 31/00

(52) U.S. Cl. ............................. 604/385.66; 604/385.29; 604/396; 2/401; 156/204; 156/263; 156/264

(58) Field of Search ................................ 604/373, 385.1, 604/385.2, 386, 389–402, 385.01, 385.19, 385.24, 385.3, 366, FOR 103, FOR 104; 2/400–408; 156/164, 204, 263–264, 229

(56) References Cited

U.S. PATENT DOCUMENTS 3,400,718 A * 9/1968 Saijo ........................... 604/394
3,860,003 A * 1/1975 Buell ........................ 604/385.2

(List continued on next page.)

FOREIGN PATENT DOCUMENTS

| EP | 0417766 | 3/1991 | |
| EP | 0446867 | 9/1991 | |
| GB | 2244422 | * 12/1991 | .................. 604/396 |
| GB | 2278993 | * 12/1994 | .................. 604/365 |
| JP | 492665 | 3/1992 | |
| JP | 4109943 | * 4/1992 | .................. 604/386 |
| JP | 4322646 | 11/1992 | |
| JP | 537219 | 5/1993 | |
| JP | 5137745 | * 6/1993 | .................. 604/394 |
| JP | 5137746 | * 6/1993 | .................. 604/396 |
| JP | 647073 | 2/1994 | |
| JP | 7289584 | 11/1995 | |
| JP | 2565498 | 10/1996 | |
| WO | 94/09736 | * 5/1994 | .............. 604/385.2 |
| WO | 28845 | 12/1994 | |
| WO | 94/28845 | * 12/1994 | .................. 604/386 |

OTHER PUBLICATIONS

English abstract of JP 3186261—1 p.*
English abstract of JP 549658—1 p.*
First page of JP 4547103—1 p.*
English abstract of WO 89/02228—1 p.*
2 pages of EP0264952.*
First page of JP 7–299092.*
Translation of Japanese 4–109,943.*
European Search Report for Application EP 95 92 8014.

*Primary Examiner*—John G. Weiss
*Assistant Examiner*—K. M. Reichle
(74) *Attorney, Agent, or Firm*—Hunton & Williams; Christopher C. Campbell

(57) ABSTRACT

An absorbent article having a main body having a front waist portion, a rear waist portion, a waist hole, two leg holes and a pair of elastic leakage protective members is disclosed. The elastic leakage protective members cooperate with the respective leg holes. The elastic leakage protective members cover at least part of the respective openings of the leg holes. Each of the elastic leakage protective members may have edge portions that form a pocket for holding body exudates.

17 Claims, 19 Drawing Sheets

U.S. PATENT DOCUMENTS

| | | | | |
|---|---|---|---|---|
| 4,427,408 A | * | 1/1984 | Karami et al. | 604/393 |
| 4,677,695 A | * | 7/1987 | Van Gompel et al. | |
| 4,695,278 A | * | 9/1987 | Lawson | 607/385.2 |
| 4,822,435 A | | 4/1989 | Igaue et al. | |
| RE33,106 E | | 11/1989 | Beckestrom | |
| 4,892,536 A | * | 1/1990 | Des Marais et al. | 604/385.2 |
| 4,938,757 A | * | 7/1990 | Van Gompel et al. | 604/346 |
| 5,019,067 A | * | 5/1991 | Simmons | 604/385.2 |
| 5,080,741 A | * | 1/1992 | Nomura et al. | 156/204 |
| 5,114,420 A | | 5/1992 | Igaue et al. | |
| 5,137,526 A | * | 8/1992 | Coates | 604/392 |
| 5,204,997 A | * | 4/1993 | Suzuki et al. | 604/385.1 |
| 5,342,583 A | * | 8/1994 | Son | 604/395 |
| 5,360,422 A | * | 11/1994 | Brownlee et al. | 604/393 |
| 5,370,634 A | * | 12/1994 | Ando et al. | 604/385.2 |
| 5,415,644 A | * | 5/1995 | Enloe | 604/385.2 |
| 5,451,217 A | * | 9/1995 | Fujioka | 604/393 |
| 5,536,350 A | * | 7/1996 | Klemp | 604/385.2 |
| 5,643,243 A | | 7/1997 | Klemp | |
| 5,669,896 A | * | 9/1997 | Kielpikowski | 604/385.2 |
| 5,690,626 A | * | 11/1997 | Suzuki et al. | 604/385.2 |
| 5,693,038 A | * | 12/1997 | Suzuki et al. | 604/385.2 |
| 5,725,518 A | * | 3/1998 | Coates | 604/393 |
| 5,725,714 A | * | 3/1998 | Fojioka et al. | 604/390 |
| 5,827,260 A | * | 10/1998 | Suzuki et al. | 604/393 |

* cited by examiner

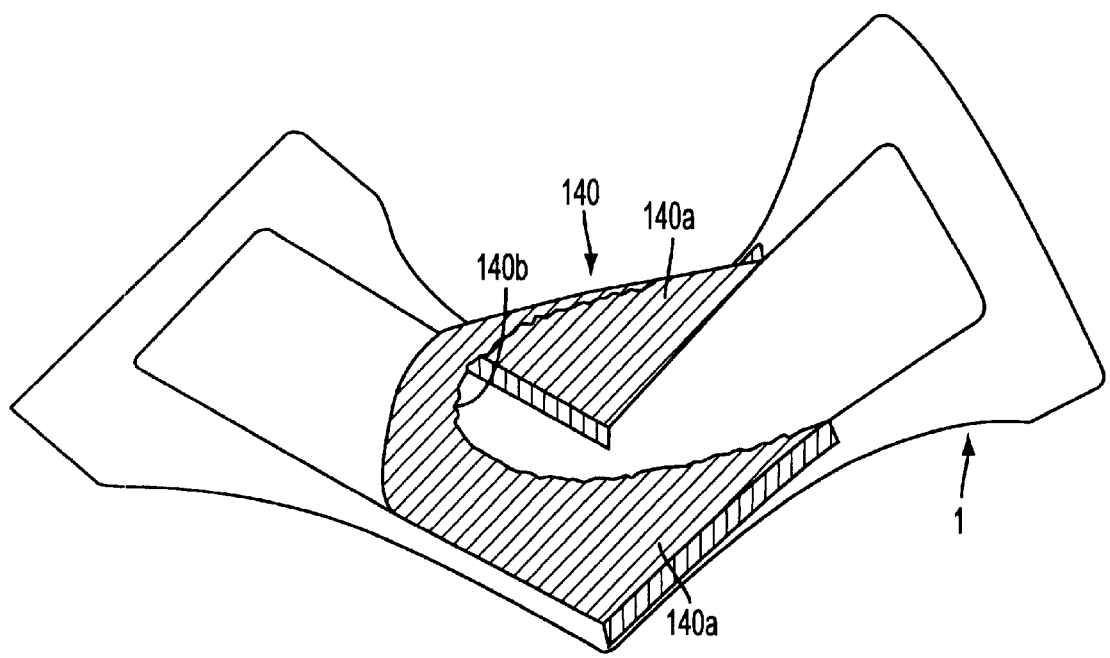
FIG. 19
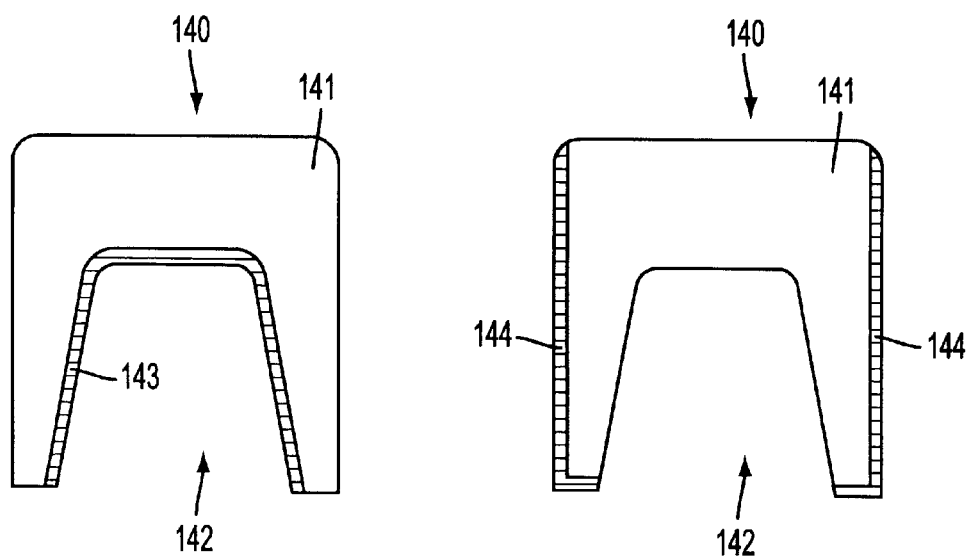
FIG. 20A
FIG. 20B

ABSORBENT ARTICLE AND METHOD OF MANUFACTURE

BACKGROUND OF THE INVENTION

1. Field of the Invention

The present invention relates to absorbent articles such as diapers for infants and adults, and sanitary articles, as well as a manufacturing method therefor.

2. Description of the Prior Art

As disclosed in Japanese Patent Laid-Open Publication 3-82467, a conventional absorbent article is composed of a liquid permeable top sheet, a liquid impermeable back, and an absorbent member. The absorbent member is disposed between the liquid permeable top sheet and the liquid impermeable back sheet. The top sheet and the back sheet are heat-bonded. In addition, to prevent body exudates from leaking out, a pair of elastic leg gathers are disposed along the peripheries of the leg holes.

The leakage protective effectiveness of disposable diapers depends, in large part, on the fit between the leg holes and the legs of the wearer. Thus, as the fit improves, the probability of leakage decreases. Consequently, as the elastic force of the gathers disposed along the leg holes or leg gathers increases, the degree of leakage decreases. However, when the elastic force is too large, the leg gathers become too tight around the legs of the wearer. Therefore, when the wearer wears the absorbent article for a long time, the wearer not only feels pain, but also may suffer skin inflammation.

These and other disadvantages of the prior art are sought to be overcome by the absorbent garment of the present invention.

SUMMARY OF THE INVENTION

It is an object of the present invention to provide an absorbent article which has excellent leakage protection while the legs of the wearer are free of excessive pressure from the leg elastics.

It is another object of the present invention to provide a method of manufacturing the above-described absorbent article.

The present invention is directed to an absorbent article comprising a main body having a front waist portion, a rear waist portion, a waist hole, and a pair of leg holes disposed between the front waist portion and the rear waist portion, and an elastic leakage protective member corresponding to each leg hole of the main body. The elastic leakage protective member interconnects both the front and rear edge portions so that at least part of the leg holes are closed.

In an alternative embodiment, the leakage protective members interconnect the front and rear side edge portions of the main body, and further include a top edge portion which extends across the front waist portion and the rear waist portion of the main body to form an annularly continuous top edge portion.

In yet another embodiment, the leakage protective members are attached to each respective side edge portion of the front and rear waist portions over substantially the entire length thereof. In such an embodiment, the leakage protective members further include leg hole openings.

As with conventional absorbent articles, the main body includes a liquid impermeable outer sheet, a liquid permeable inner sheet, and an absorbent member disposed therebetween. The front waist portion and a rear waist portion may be integrally formed with one another. Alternatively, the front waist portion and the rear waist portion may be separately prepared and then joined. The rear waist portion and the front waist portion are connected at the crotch portions thereof.

In this specification, the term "leakage protective member" will be understood to include sheet members which are disposed on both sides of the above-described main body and has an elastic sheet forming at least part of the periphery of a leg hole and prevents body exudate from leaking. The elastic leakage protective member may have a variety of forms, such as a standing cuff disposed at each side of the main body or a pocket for holding body exudate.

Experimental results show that due to the elasticity of the elastic leakage protective member, the elastic leakage protective member satisfactorily contains exudates when it closes more than $2/3$ of the opening of the leg hole.

The elastic leakage protective member may have a slit which has a predetermined length and which extends from a portion which constitutes part of the periphery of the leg hole. The slit allows the elastic leakage protective member to have a large opening. Urine and excrement are sealed by the elastic leakage protective member which is disposed at a lower crotch portion and follows the motion of the wearer. The elastic leakage protective member is preferably secured to the crotch portion of the main body.

An absorbent article of this type may be manufactured by forming a first series of front waist portions and second series of rear waist portions along an assembly line. Each series of waist portions is formed from continuous strips of top sheet material and back sheet material, with absorbent members deposited between the sheets at predetermined intervals. The elastic leakage protective member or members may be deposited on one of the waist portions either by laying the material on the waist portions in continuous strips or by pre-forming assemblies which are deposited on the waist portions at predetermined intervals. Once the elastic leakage protective members are placed on one waist portion, the other waist portion is laid on top of it, thus sandwiching the elastic leakage protective members between the first and second waist portions. The several components may then be attached to each other by bonding the waist portions at the crotch region and severing the completed article from the continuous strips of material.

An article of this type may also be manufactured by following the above steps, and also interconnecting the side edges of the waist portions by attaching the edges of each waist portion to the elastic assembly or members, in addition to attaching the waist portions to one another at the crotch.

Another process for producing an absorbent article of this type may be to assemble an article body formed from a single continuous top sheet and a single continuous back sheet, between which are sandwiched absorbent members placed at predetermined intervals. The elastic leakage protective members, which may be either continuous strips of material or pre-formed assemblies, are deposited on the article body. The individual article is made by folding the continuous sheets over on itself, thereby sandwiching the elastic member, and bonding the article at predetermined points to affix the elastic member between the waist portions, and severing the article from the continuous sheets. Such a construction does not require attaching the two waist portions to one another at the crotch because they are formed from the same continuous sheets of material.

These and other objects and advantages of the disposable absorbent garment and method of manufacturing will become apparent when the description is read in conjunction with the drawing figures.

BRIEF DESCRIPTION OF THE DRAWINGS

FIG. 19 is an exploded perspective view showing an absorbent article according to yet another preferred embodiment;

FIG. 20A is a front view of an elastic leakage protective member for use with the absorbent article of FIG. 19;

FIG. 20B is a rear view of the elastic leakage protective member of FIG. 20A;

DETAILED DESCRIPTION OF THE PREFERRED EMBODIMENTS

Figure 1:
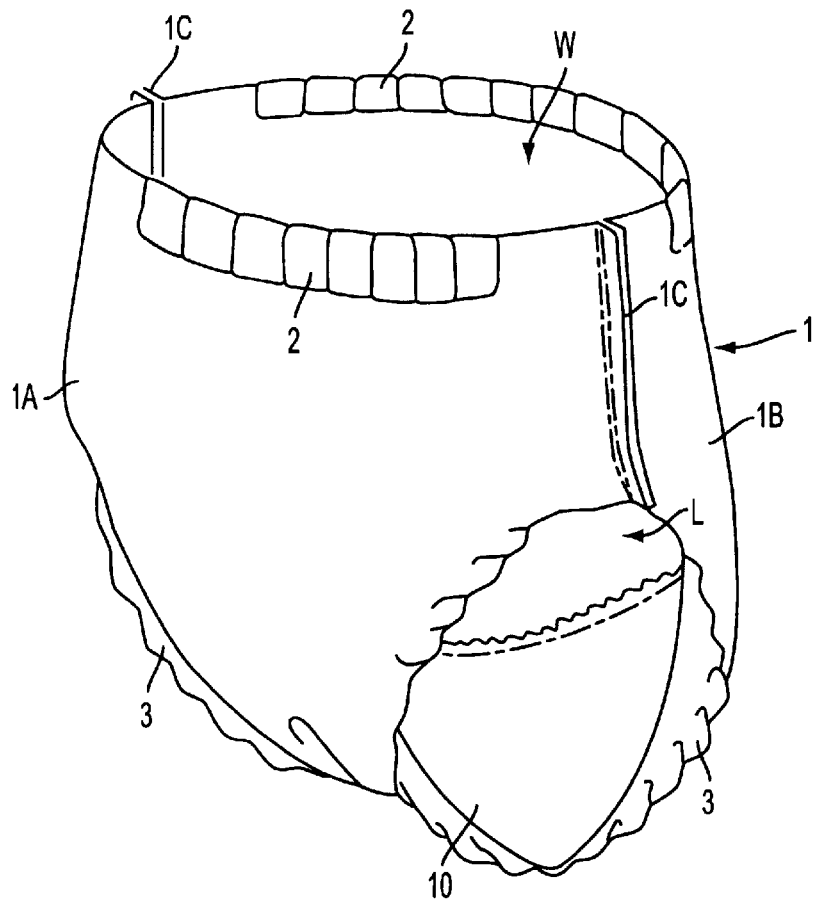
FIG. 1 is a perspective view showing an absorbent article according to a first preferred embodiment.

With reference to FIG. 1, a tape-less type diaper absorbent article according to a first preferred embodiment in the state in which a wearer wears the absorbent article is depicted. Waist hole W and two leg holes L are formed on a main body 1. An elastic leakage protective member 10 is disposed at a lower portion of each of the leg holes L so that it covers at least part of the leg holes L (in this embodiment, around ⅔ of the leg holes). A waist gather 2 and a leg gather 3 may optionally be disposed along the waist hole W and each of the leg holes L so as to provide them with elasticity.

Figure 2:
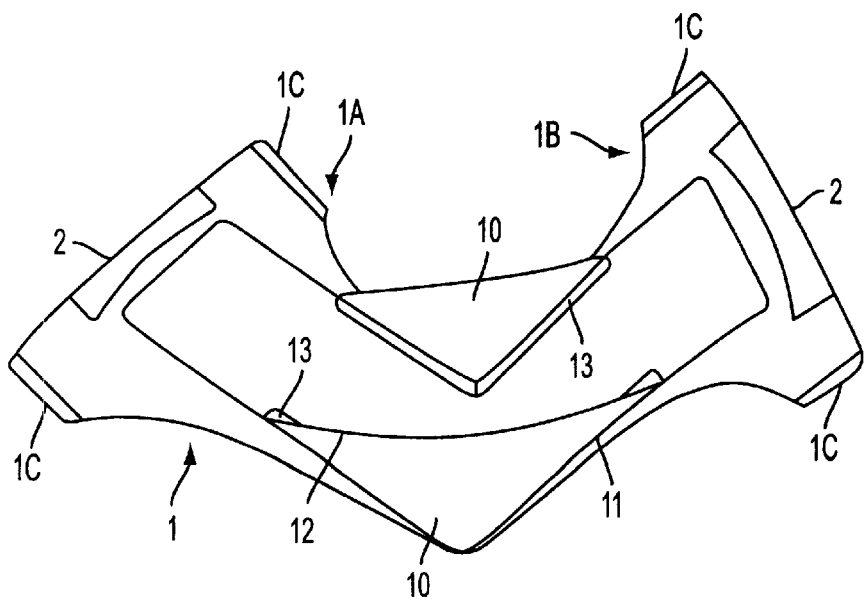
FIG. 2 is an exploded perspective view showing the absorbent article shown in FIG. 1.

FIG. 2 is an exploded view of FIG. 1. In FIG. 2, the main body 1 is of the conventional pants-type having a liquid permeable top sheet, a liquid impermeable back sheet, and an absorbent member disposed therebetween. The main body 1 has a front waist portion 1A and a rear waist portion 1B. The front waist portion 1A covers the abdomen of the wearer. The rear waist portion 1B covers the hips. The main body 1 is formed in a rectangular shape of which the longitudinal center portion is narrowed. Each edge of the front waist portion 1A and rear waist portion 1B are connected with respective connection portions 1C. Alternatively, the preferred embodiment may be adapted to a tape-type absorbent article. In this case, tapes which are detachably connected to the front waist portion 1A are disposed at both edges of the rear waist portion 1B. Since the structure of the main body 1 is basically the same as the structure of conventional absorbent articles, a detailed description of the main body 1 is omitted. In addition, for simplicity, FIG. 2 does not show the leg gathers 3.

A pair of elastic leakage protective members 10 are preferably disposed on both sides of the center portion (i.e., the crotch portion) of the main body 10. Each of the elastic leakage protective members 10 approximates an isosceles triangle, but due to manufacturing tolerances, may have either a V-shaped or U-shaped lower edge 11 and a straight or arc-shaped upper edge 12. Connection region 13 extending from lower edge 11 is folded and connected to the inner front surface of the crotch portion of the main body 1 with a suitable bonding agent, such as a hot-melt type bonding agent.

The elastic leakage protective member 10 is preferably made from a material which is comfortable to the touch, has the proper elasticity, high flexibility, and good leakage resistance. Examples of such materials include nonwoven fabrics with suitable flexibility and elasticity and composite materials of non-woven fabric and elastic. One suitable non-woven fabric consists of an alternating fabric of polyester, polypropylene, or the like with a carded web which contains conjugated fibers in a water stream and then heat-shrinking the resultant substance. Preferable examples include elastic composite substances of non-woven fabrics and elastic films, composite substances of non-woven fabrics and melt-blown elastics, and composite substances of non-woven fabrics and net-shaped elastics. Although an elastic film may be used since it directly touches the skin of the wearer, the elastic film should preferably be used along with a non-woven fabric.

A more preferable example of the elastic leakage protective member is a material having air permeability. When necessary, a plurality of small air pores are preferably formed at the upper portion of each of the elastic leakage protective members so as to allow breathability.

In addition, the elastic leakage protective members 10, which cover part of the respective leg holes L, do not prevent the legs of the wearer from passing therebetween due to the elasticity thereof. In use, the elastic leakage protective members 10 complement the fit around the legs along with the leg gathers 3.

In the embodiment shown in FIGS. 1 and 2, connection region 13 is preferably formed by inwardly folding part of each of the elastic leakage protective members 10. Alternatively, connection region 13 may be formed by outwardly folding and then bonding to main body 1.

Figure 3:
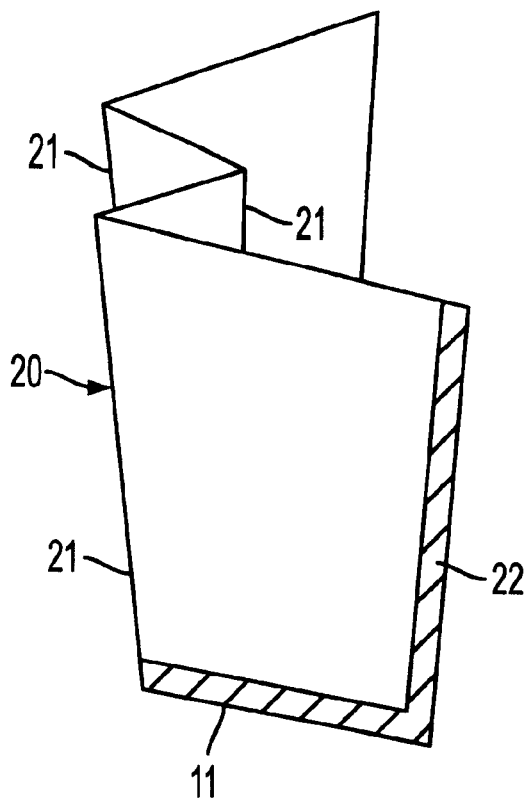
FIG. 3 is a perspective view showing an elastic leakage protective member for use with an absorbent article according to another preferred embodiment.

As a further alternative, as shown in FIG. 3, leakage protective members 20 may be formed from a nearly rectangular or trapezoidal sheet-shaped material folded in a zigzag pattern along three substantially parallel folding lines 21. The elastic leakage protective members 20 are connected to the main body 1 with a bonding agent 22, such as a hot-melt type bonding agent, in such a manner that the bonding agent 22 is preferably applied the full length of the lower edge of each of the elastic leakage protective members 20 and the side edge of the segment disposed at both ends thereof. Since the length of the folded elastic leakage protective members 20 is longer than the length of the flat elastic leakage protective members 10 shown in FIGS. 1 and 2, the degree of expansion is increased in the embodiment of FIG. 3.

Figure 4A:
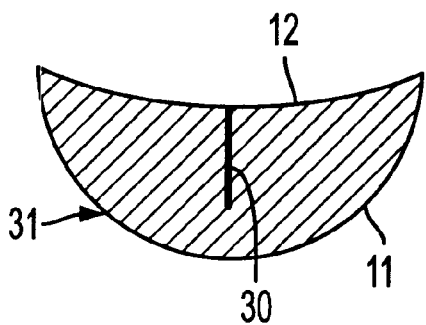
FIGS. 4A and 4B are plan views showing elastic leakage protective members for use with an absorbent article according to another preferred embodiment.
Figure 4B:
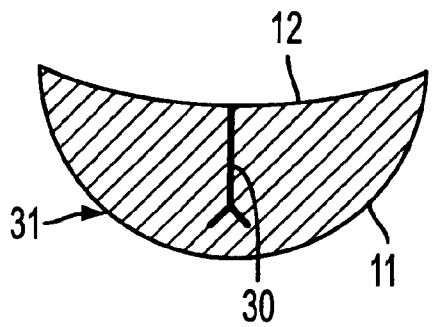

FIGS. 4A and 4B show elastic leakage protective members according to another preferred embodiment. A slit 30 is formed in a leakage protective member 31 formed from an elastic material. Slit 30 extends from the center position of an upper edge 12 of the leakage protective member 30 to a lower edge thereof. In the embodiment shown in FIG. 4A, slit 30 is a straight line. In the embodiment shown in FIG. 4B, slit 30 branches at the lower position thereof In use, when a leg of the wearer extends through the leg hole L, slit 30 allows the upper portion of the elastic leakage protective member 31 to open. Thus, even if the elastic leakage protective member 31 covers a large part of the leg hole L, the elastic leakage protective member 31 does not prevent the leg of the wearer from passing through the leg hole L. In addition, since the elastic leakage protective member 31 contacts the leg along a substantial portion of the periphery of the leg hole L, the fit of the absorbent article improves.

Figure 5:
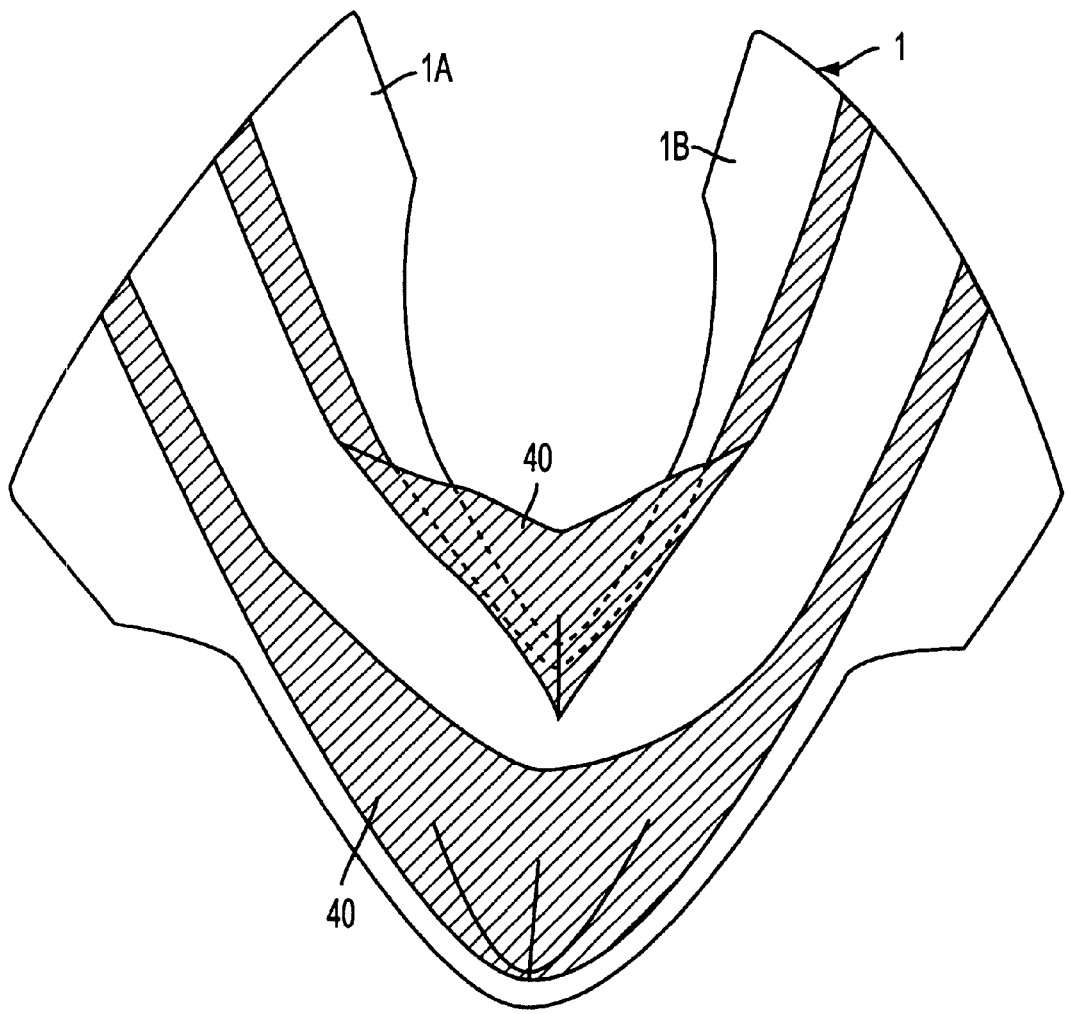
FIG. 5 is a perspective view showing an absorbent article according to another preferred embodiment.
Figure 6:
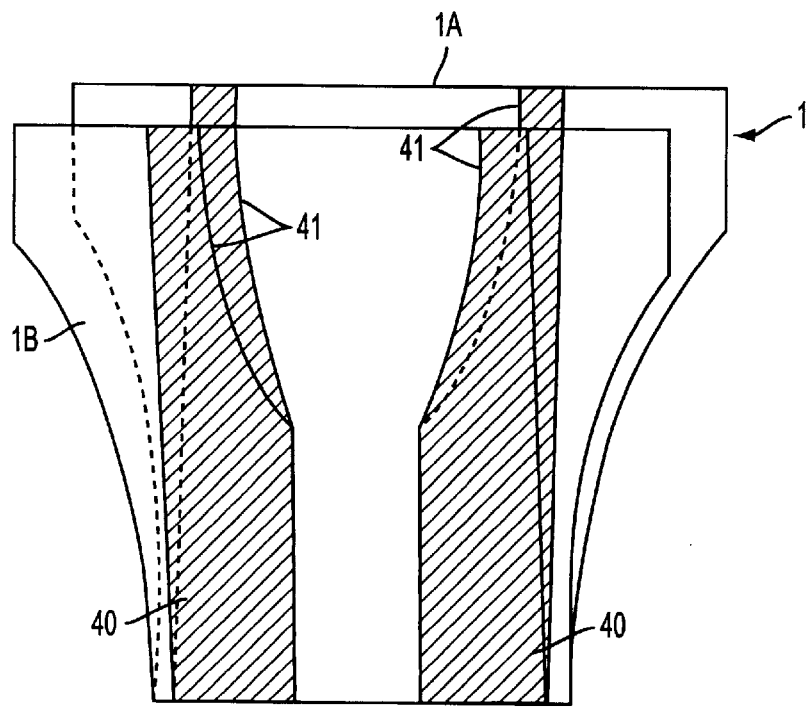
FIG. 6 is a schematic diagram of the elastic leakage protective member in the absorbent article of FIG. 5.

FIGS. 5 and 6 show an absorbent article according to another preferred embodiment. In this embodiment, each of elastic leakage protective members 40 is made from an elongated strip-shaped elastic material. Each of the elastic leakage protective members 40 is widest at the center position of the crotch of the main body 1. In other words, the width of the elastic leakage protective member 40 near the waist hole is smaller than the width near the crotch. The elastic leakage protective member 40 is preferably cut out on both side edges thereof (the cut-outs illustrated by numeral 41) for a predetermined length. In the embodiment shown in FIG. 6, the elastic leakage protective members 40, are attached to the interior of main body 1 (shown in phantom lines) between front waist portion 1A and rear waist portion 1B (also shown in phantom lines), and are connected at an outer edge portion of the main body 1. However, with the elastic leakage protective members 40, as shown in FIG. 5, when the leg holes are enlarged, edge portions which are not bonded to the main body 1 are raised and form cuffs which cover at least part of the leg holes as with the above-described embodiment.

FIG. 5 shows elastic leakage protective members 40 disposed to the main body 1 with the inner edge portions thereof. For simplicity, the two elastic leakage protective members 40 are shown in the same drawing. Elastic leakage protective members 40 are preferably substantially the same as one another.

As shown in FIG. 6, elastic leakage protective members 40 are preferably attached to the main body 1 so that each open side thereof faces inwardly. In this case, the standing portions of the elastic leakage protective members 40 are disposed laterally inside the connection line of the main body 1.

Figure 7:
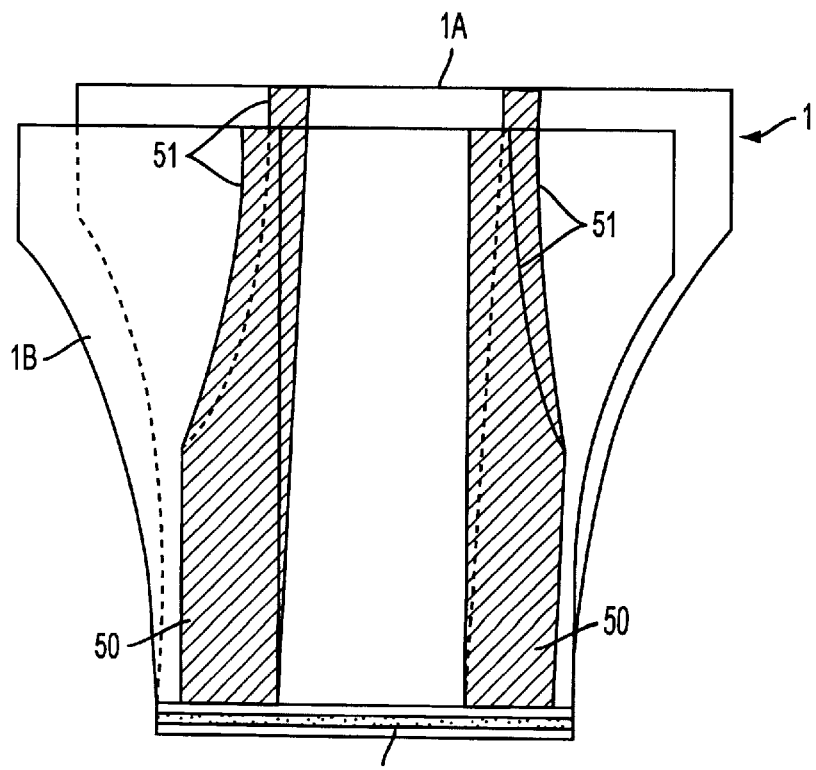
FIG. 7 is a schematic diagram of another embodiment of an elastic leakage protective member in an absorbent article similar to FIG. 5.

In the embodiment shown in FIG. 7, the main body 1 has a front waist portion 1A and a rear waist portion 1B connected at 1D in the crotch (all shown in Phantom lines). The elastic leakage protective members 50 are attached to the interior of the main body 1 between front waist portion 1A and rear waist portion 1B in such a manner that cut-out portions 51 (which are substantially the same as those shown in FIGS. 5 and 6) face outwardly. In use, the elastic leakage protective members 50 rise to prevent body exudate from leaking.

The method of manufacturing the absorbent article of FIG. 7 is described in more detail below in connection with FIG. 12. There, a first assembly positions absorbent members between the back sheet and the top sheet web material at predetermined intervals, and a second assembly positions the leakage protective members. Each front waist portion 1A and each rear waist portion 1B are connected at a connection portion 1D.

Figure 8:
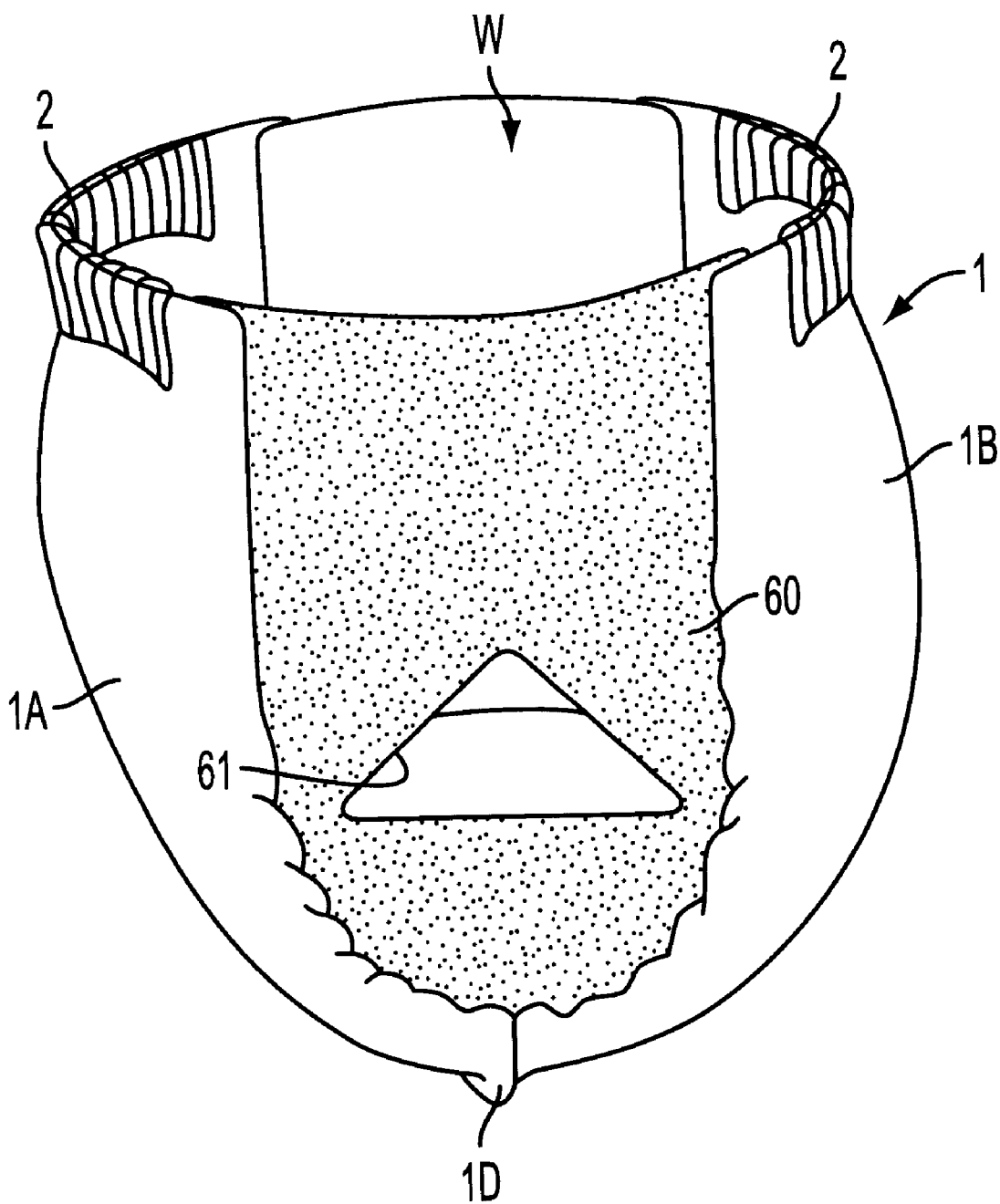
FIG. 8 is a perspective view showing an absorbent article according to another preferred embodiment.

FIG. 8 shows an absorbent article according to another preferred embodiment. In this embodiment, a pair of elastic leakage protective members 60 are disposed to a main body 1 to connect the front waist portion 1A to the rear waist portion 1B. The upper edges of the front waist portion 1A, the rear waist portion 1B, and the elastic leakage protective members 60 are connected in a ring shape and thereby form a waist hole W. Each of the elastic leakage protective members 60 has an opening 61 approximating an isosceles triangle. Opening 61 forms a leg hole.

In this structure, each of the elastic leakage protective members 60 functions as a cuff which fits around the periphery of the leg of the wearer and prevents body exudate from leaking. In addition, the elastic leakage protective member 60 functions as a leakage protective band connecting the front and the rear waist portions 1A and 1B at their side positions. Elastic leakage protective member 60 improves the fit of the absorbent article without increasing the elastic forces about the wearer's legs.

Figure 9A:
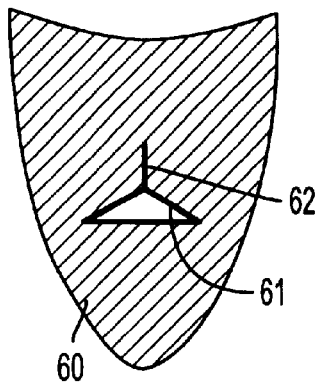
FIGS. 9A–11B are plan views showing elastic leakage protective members according to further preferred embodiments for use with the absorbent article shown in FIG. 8.

A slit 62 may optionally upwardly extend from the apex of the opening 61 as shown in FIG. 9A. Slit 62 also facilitates tearing open the elastic leakage protective member 60 when the wearer desires to remove the absorbent article. If the required tearing force is large, a perforation may optionally extend from the apex of the opening 61 to the upper edge of the elastic leakage protective member 60.

When the height of the triangular opening 61 is properly selected, the sum of the three sides of the triangle can be selected from a wide range.

Figure 9B:
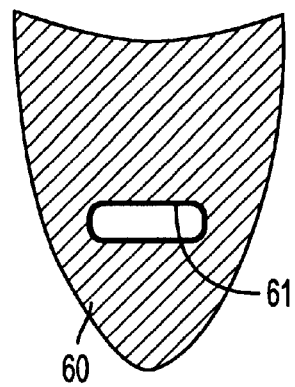

Alternatively, as shown in FIG. 9B, an elliptic leg hole 61 may be provided.

Figure 10A:
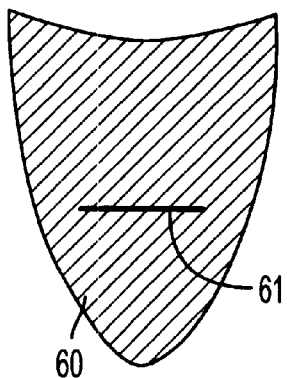
Figure 10B:
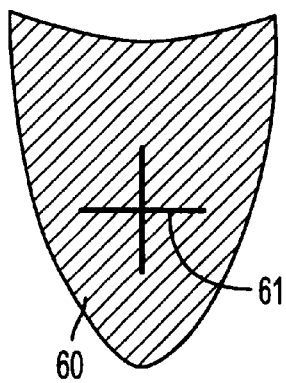
Figure 10C:
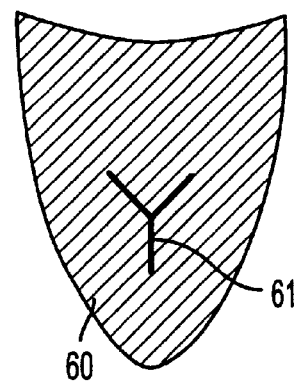

Moreover, as shown in FIGS. 10A, 10B, and 10C, the opening 61 may be formed as slits configured in a straight line, a cross, or a Y, respectively.

Figure 11A:
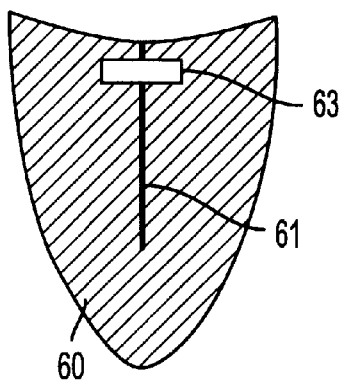
Figure 11B:
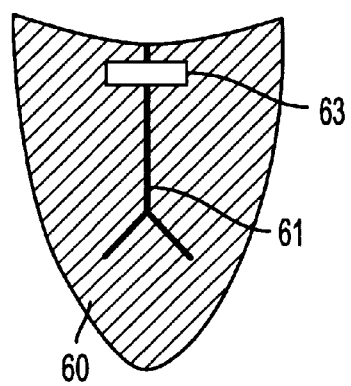

When the opening 61 is a slit, as shown in FIGS. 11A or 11B, one end of slit 61 may optionally extend to the upper edge of elastic leakage protective member 60 to the waist hole. The upper edge is closed with a closing device 63 such as tape or a VELCRO fastener.

In addition, the present invention provides a method for manufacturing the absorbent article of FIG. 7. FIG. 12 shows the principal steps of a manufacturing process for manufacturing an absorbent article according to a preferred embodiment.

Figure 12:
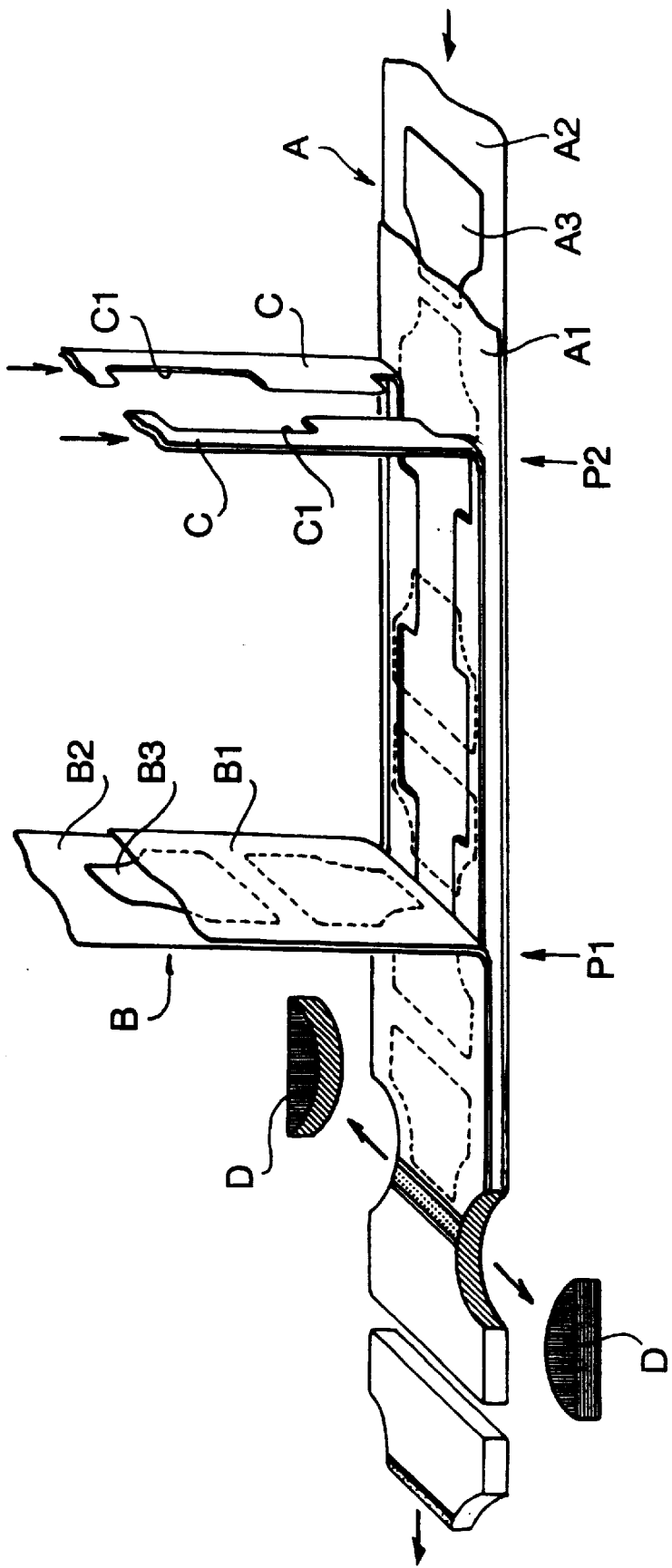
FIG. 12 is a perspective view of the manufacturing steps of making the absorbent article shown in FIG. 7.

With reference to FIG. 12, A represents a first assembly which eventually forms the front portion of the absorbent article. B represents a second assembly which eventually forms the rear portions of the absorbent article. The first assembly layers top sheet A1, absorbent articles A3, and back sheet A2. The absorbent articles A3 are disposed between the top sheet A1 and the back sheet A2 at predetermined intervals. The first assembly A is conveyed at a predetermined speed in the direction of the arrow. Second assembly B layers top sheet B1, absorbent articles B3, and back sheet B2. The absorbent articles B3 are disposed between the top sheet B1 and the back sheet B2 at predetermined intervals. The second assembly B is conveyed in the direction of the arrow in synchronization with the first assembly A.

The first assembly A and the second assembly B are layered by, e.g., a guide roller in such a manner that each absorbent article A3 faces each absorbent article B3 at position P1 of the conveying path. At a position P2 (upstream of the position P1), a pair of opposed sheet members C, which become elastic leakage protective members, are continuously supplied on top sheet A1 of the first assembly A. Each of the sheet members C is preferably formed by folding a web of material along the longitudinal axis thereof. Openings C1 are preferably formed from the folded edge to nearly the opposite free edge. Sheet members C are supplied to both edges of the first assembly in such a manner that the folded edges thereof face each other. A hot-melt type bonding agent is applied to sheet members C at predetermined positions.

When the first assembly A and the sheet member C placed thereon reach the position P1, the second assembly B is layered on the sheet member C. The resultant layered members are supplied to a heat-bonding unit (not shown) which bonds the layered members with a hot-melt type bonding agent. Finally, portions D are cut out to form leg openings and each absorbent article is separated.

The above-described manufacturing method is generally referred to as longitudinal manufacturing. Since each cover stock material is conveyed in parallel with the side edge of each product, the absorbent articles can be manufactured at substantially high speeds. Thus, manufacturing is improved and the costs correspondingly reduced.

Figure 13:
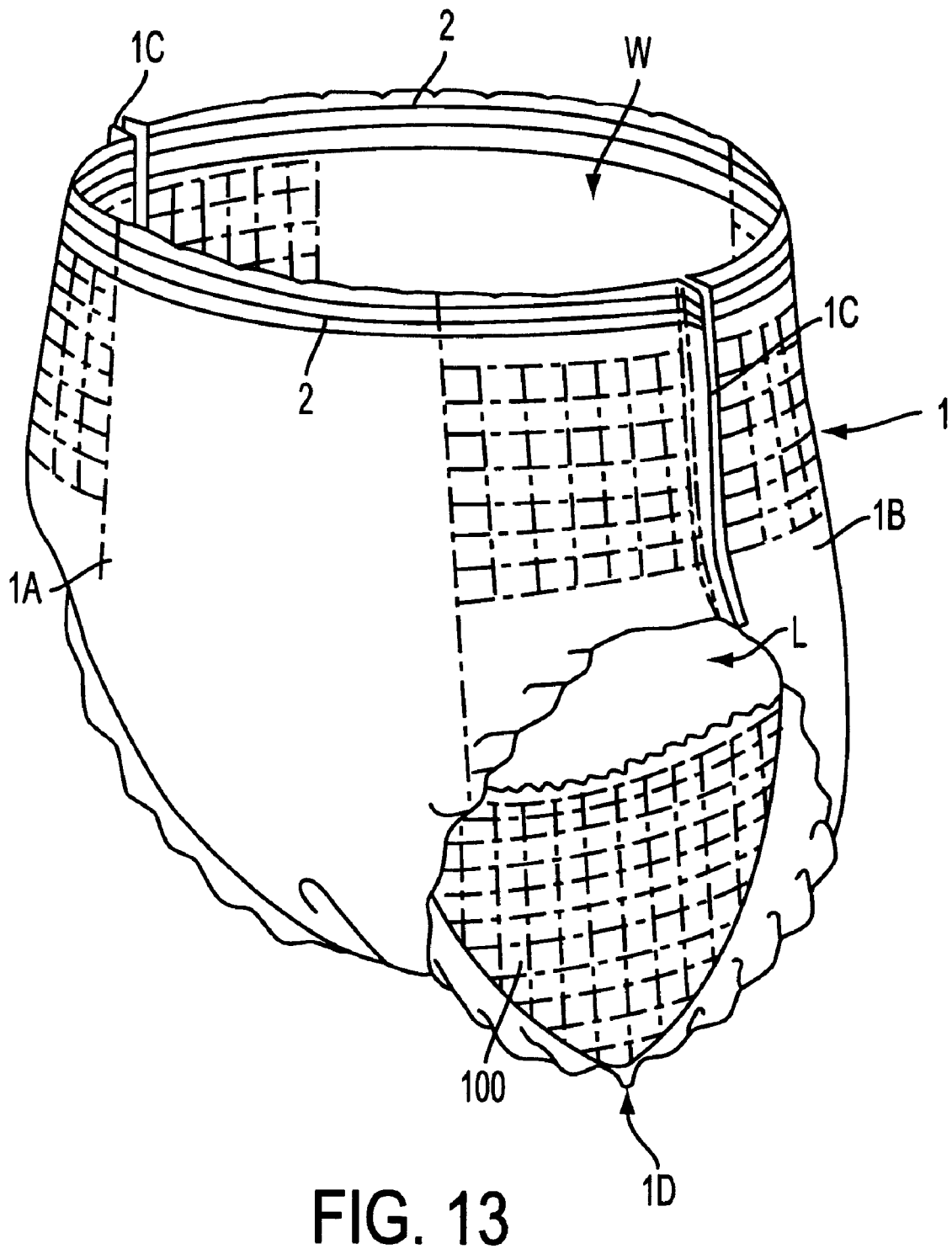
FIG. 13 is a perspective view showing an absorbent article according to another preferred embodiment.

FIG. 13 is a perspective view showing an absorbent article in the form of a tape-less type diaper according to another preferred embodiment. Referring to FIG. 13, which depicts the configuration of the absorbent article in use, waist hole W and two leg holes L are formed in main body 1. A pair of elastic leakage protective members 110a are disposed in such a manner that they cover about half of the lower portion of the respective leg holes. In addition, an elastic waist gather 2 is disposed along the waist hole W.

Figure 14:
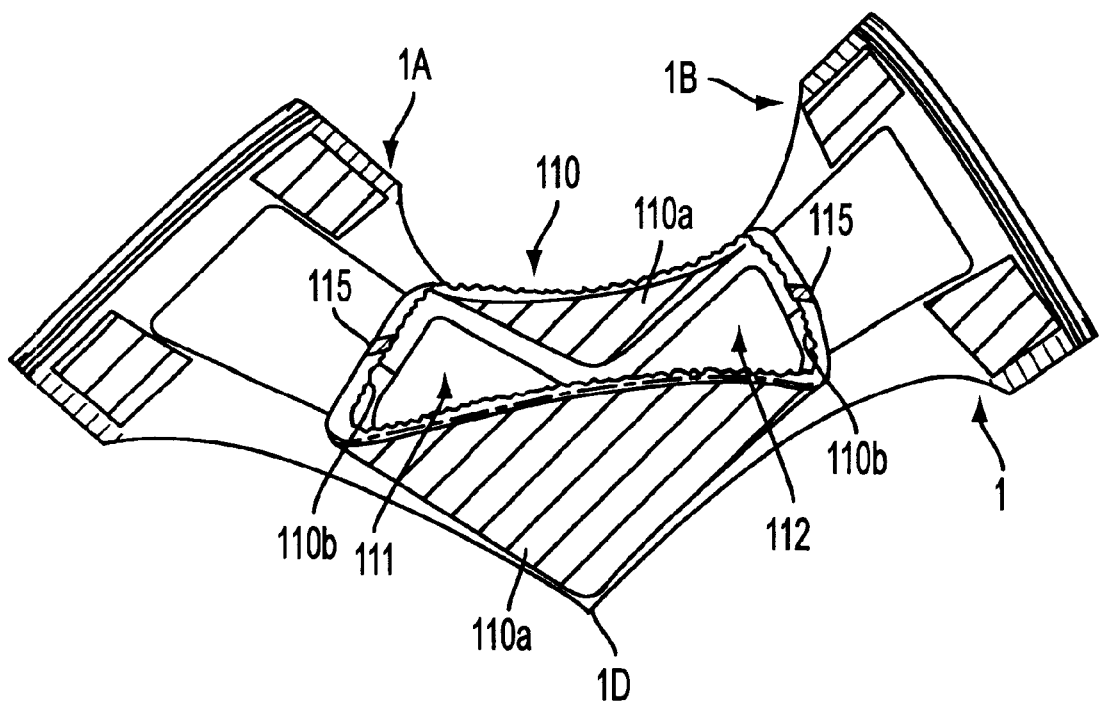
FIG. 14 is an exploded perspective view showing the absorbent article of FIG. 13.

FIG. 14 is an exploded view of the absorbent article of FIG. 13. The main body 1 has a liquid permeable top sheet, a liquid impermeable back sheet, and an absorbent member disposed therebetween. The main body 1 further has a front waist portion 1A and a rear waist portion 1B. The front waist portion 1A covers the abdomen. The rear portion 1B covers the hips. The main body 1 is formed in a substantially rectangular shape of which the longitudinal center portion is narrowed. The edges of the front and rear waist portions 1A, 1B are connected at 1C (FIG. 13) and at 1D in the crotch. Alternatively, the present invention can be applied in a tape-type absorbent article. In this case, tapes are disposed at both edges of the rear portion of the main body 1. In addition, the front and rear waist portions 1A, 1B may be integrally structured without the connection portions 1D. Since the structure of the main body 1 is basically the same as the structure shown in FIG. 1, a detailed description thereof is omitted.

An elastic leakage protective member 110 is disposed at the center (namely, the crotch) of the main body 1. The elastic leakage protective member 110 is formed from an elastic composite sheet. The elastic composite sheet preferably includes a non-woven fabric and net-shaped elastic. The elastic leakage protective member 110 approximates the shape of a prism. The bottom surface and two inclined surfaces of the elastic leakage protective member 110 have openings 111 and 112, respectively. The elastic leakage protective member 110 has first members 110a disposed on two opposite sides of the prism-shaped structure and second members 110b which connect the first members 110a. Lower edges of the first members 110a and the second members 110b are folded inwardly. The elastic leakage protective member 110 is connected to the inner surface of the crotch of the main body 1 with a suitable bonding agent such as a hot-melt type bonding agent. Reference numeral 115 denotes a connection between the first portion 110a and the second portion 110b on respective front and rear sides of the absorbent article.

The elastic leakage protective member 110 is preferably made from the same material as that of the embodiment shown in FIGS. 1 and 2.

Although, the elastic leakage protective member 110 covers part of the leg holes L, its elasticity allows the leg of the wearer to pass relatively easily therethrough. In use, the elastic leakage protective member 110 complements the leg gathers 3 to create a secure fitting absorbent article.

In addition, since the upper edge portions of the first and second members 110a, 110b engage the crotch of the wearer, the elastic leakage protective member 110 not only provides an excellent fit, but improved leakage containment. Moreover, openings 111 and 112 provide paths for guiding body exudate to the main body 1.

Figure 15:
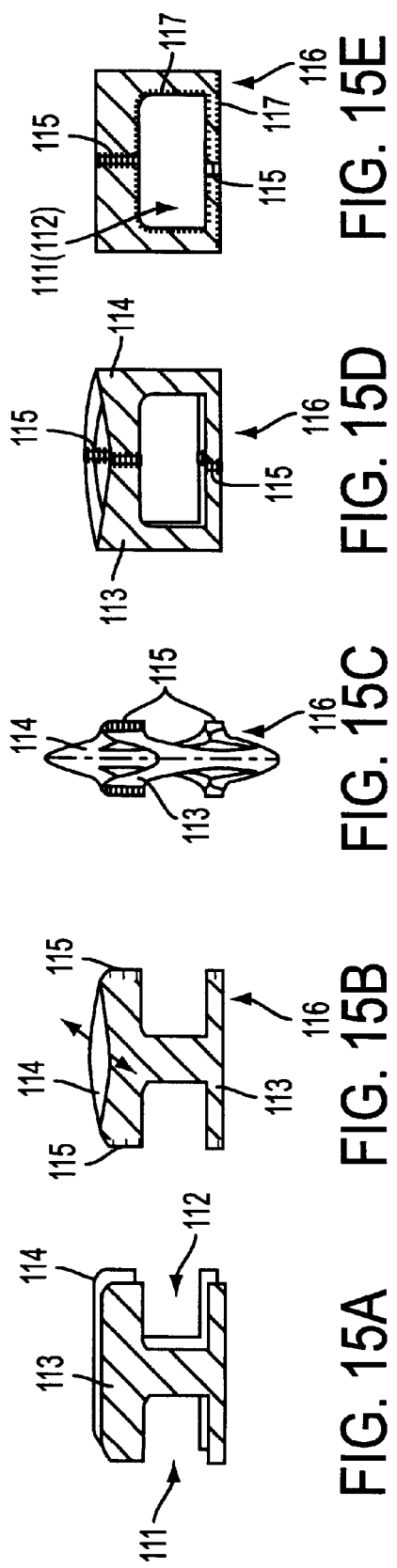
FIG. 15 depicts the steps for manufacturing an elastic leakage protective member for use with the absorbent article shown in FIGS. 13 and 14.
Figure 16:
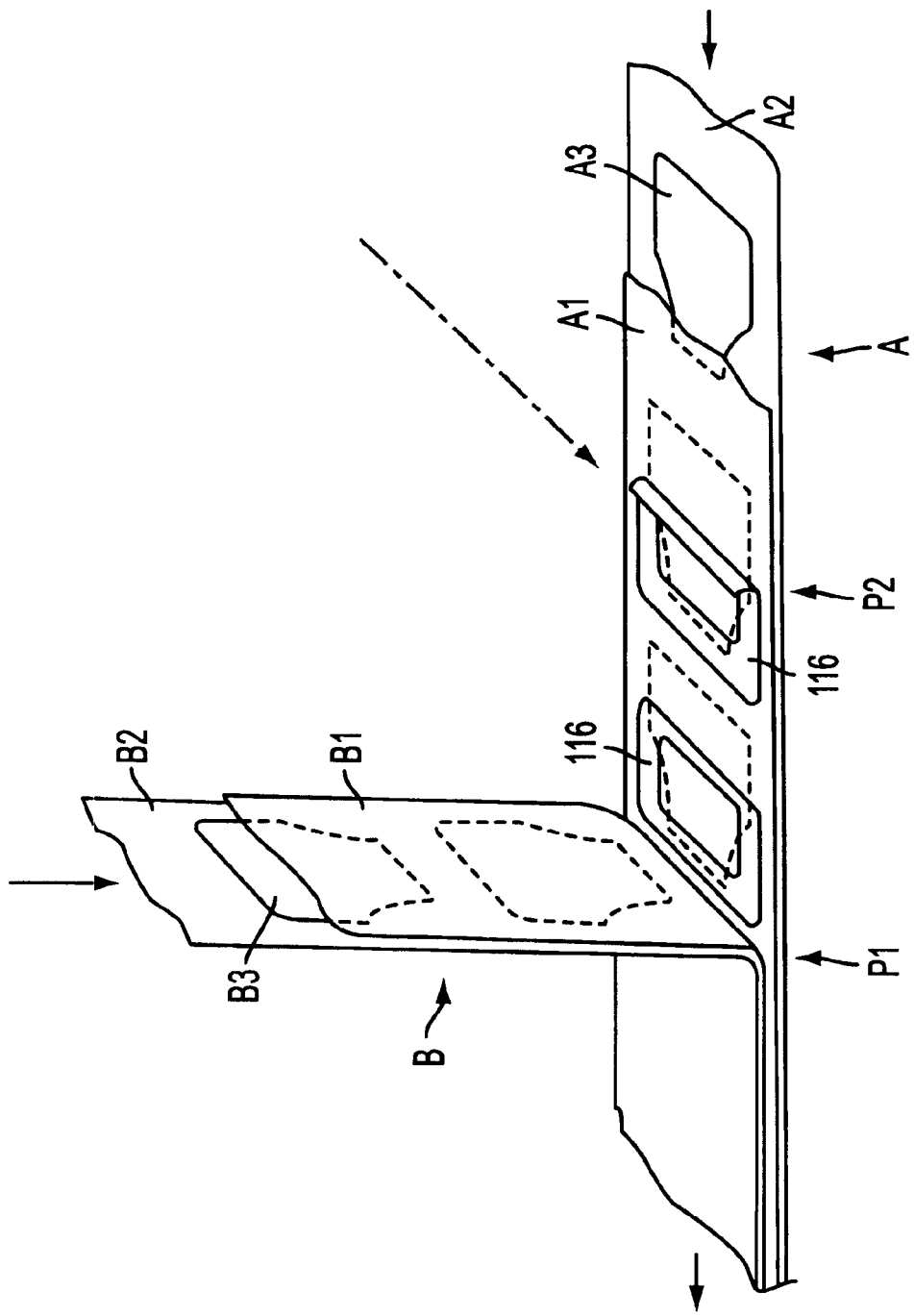
FIG. 16 is a perspective view showing the manufacturing step of placing the elastic leakage protective member of FIG. 15 to the body of an absorbent article.

FIGS. 15 and 16 show a manufacturing process for an absorbent article having the elastic leakage protective member 110 shown in FIG. 14. Two I-shaped sheet members 113 and 114 which have openings 111 and 112 extending from both side edges to the center portion are prepared. The sheet members 113 and 114 are layered (at step A). Thereafter, the sheet members 113 and 114 are connected at edge portions 115 to form a cylindrical subassembly 116 (at step B). Next, the sheet members 113 and 114 are pulled in opposite directions as shown by the arrows until connection portions 115 face each other (at steps C and D). Then, a hot-melt type bonding agent 117 is applied to the periphery of the openings 111 and 112, and the lower edge of the subassembly 116 (at step E).

Alternatively, if connection portions 115 can be exposed to both sides of the main body 1, at step A of FIG. 15, substantially ring-shaped members with openings at the center positions thereof are used as the sheet members 113 and 114. The process then advances to step E, where a hot-melt type bonding agent is applied to the sheet members 113, 114 at predetermined positions.

The subassembly is supplied to the manufacturing line shown in FIG. 16. In FIG. 16, A represents a first assembly which eventually becomes the front waist portion of the absorbent article. B represents a second assembly which eventually becomes the rear waist portion of the absorbent article. The first assembly layers top sheet A1, absorbent articles A3, and back sheet A2. The absorbent articles A3 are disposed between the top sheet A1 and the back sheet A2 at predetermined intervals. The first assembly A is conveyed at a predetermined speed in the direction of the arrow. Likewise, the second assembly B layers top sheet B1, absorbent articles B3, and back sheet B2. The absorbent articles B3 are disposed between the top sheet B1 and the back sheet B2 at predetermined intervals. The second assembly B is conveyed in direction of the arrow in synchronization with the first assembly A.

The first assembly A and the second assembly B are layered by, e.g., a guide roller so that each absorbent article A3 faces each absorbent article B3 at position P1 of the conveying path. At position P2, the subassemblies 116 obtained in the process shown in FIG. 15 are supplied in synchronization with the first assembly A. The subassemblies 116 are successively placed on the top sheet A1 of the first assembly A in synchronization with the absorbent members A3. Thus, when each of the subassemblies 116 reaches the position P1, the second assembly B is layered on the subassembly 116. Consequently, the subassembly 116 is sandwiched between the two assemblies A and B. A hot-melt type bonding agent is then applied to predetermined positions of the assemblies A and B.

The three layered members are then delivered to a suitable cutting apparatus for forming the leg openings, and finally to an apparatus for separating these members into absorbent articles (these steps are not shown). Thus, final products are obtained.

Figure 17:
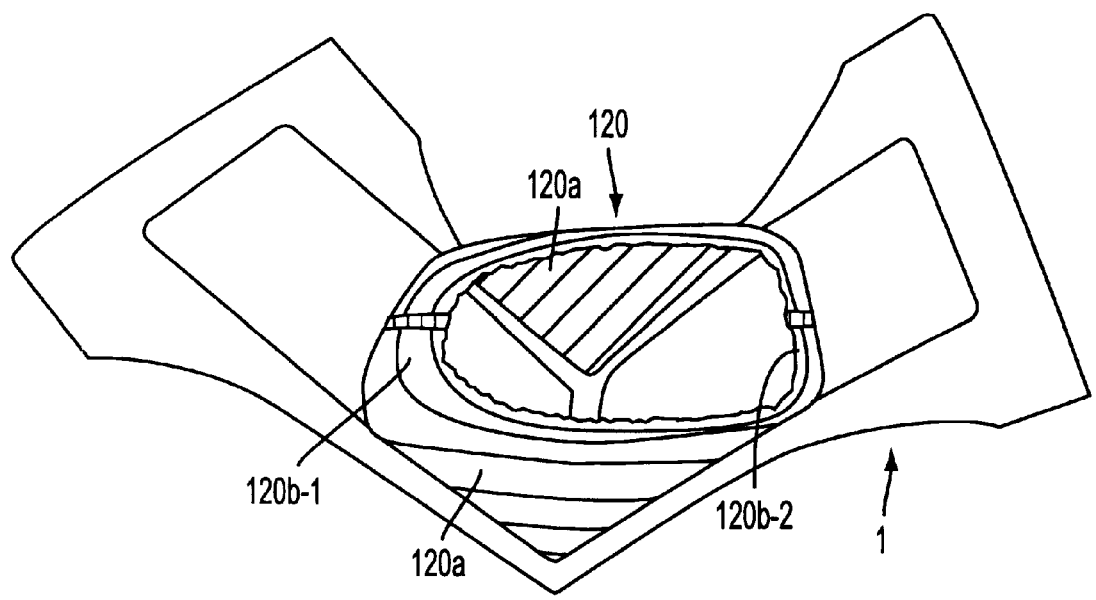
FIG. 17 is an exploded perspective view showing an absorbent article according to another preferred embodiment.

FIG. 17 shows an absorbent article according to another preferred embodiment. In FIG. 17, an elastic leakage protective member 120 is disposed in the main body 1 of the absorbent article. Portion 120b-1 corresponding to portion 110b (in FIG. 14) is wider than portion 120b-2 corresponding to portion 110b (in FIG. 14). The wider portion 120b-1 forms a large pocket for holding body exudate along with the inner surface of the main body 1 disposed therebelow.

Figure 18:
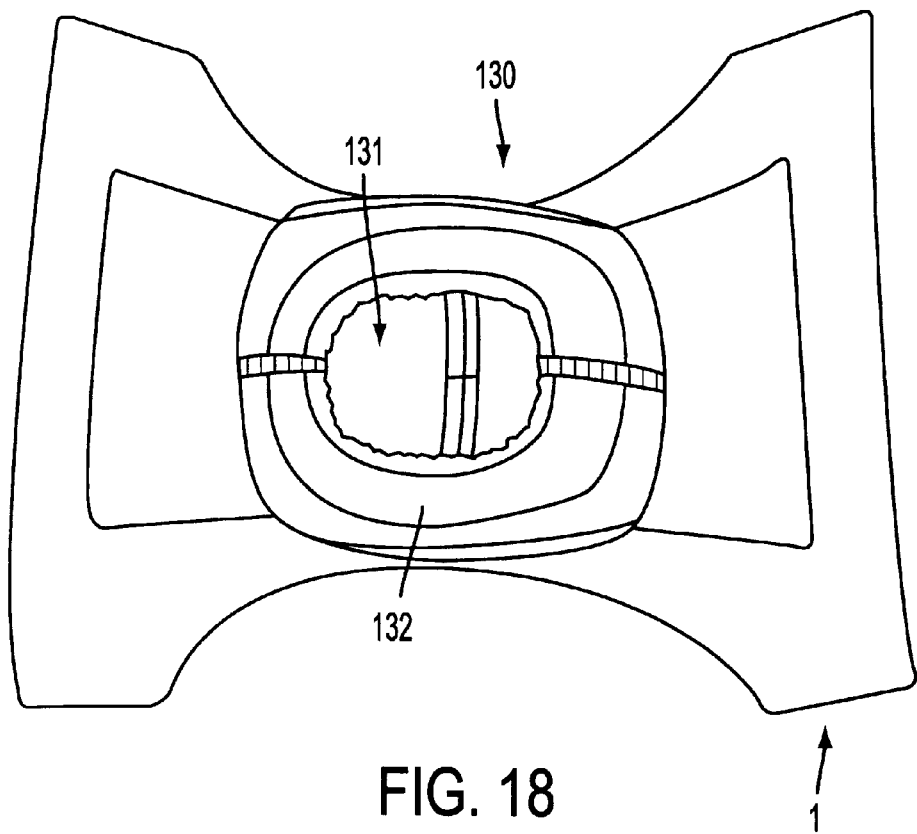
FIG. 18 is an exploded perspective view showing an absorbent article according to another preferred embodiment.

FIG. 18 shows an absorbent article according to another preferred embodiment. In FIG. 18, the upper edge of an elastic leakage protective member 130 extends inwardly, thereby forming a flange member 132 having an opening 131 at the center portion thereof. The opening 131 collects and holds body exudate. The entire elastic leakage protective member 130 functions as a pocket for holding the body exudate.

FIG. 19 shows an absorbent article according to another preferred embodiment. In FIG. 19, an elastic leakage protective member 140 is attached to a main body 1 and comprises two first portions 140a and one second portion 140b. The first portions 140a are disposed on both edges of the crotch region of the main body 1. The second portion 140b is connected to the first portions 140a.

First portions 140a and second portion 140b are formed from a single elastic sheet material. The elastic leakage protective member 140 is structured by forming a nearly rectangular sheet member 141 with a suitable elasticity in a U-shape as a result of cut-out portion 142. Bonding agents 143 and 144 are applied as shown on the front surface (FIG. 20A) and along an outer periphery on the rear surface (FIG. 20B). The sheet member 141 is the placed at the center portion of the main body 1, and bonded to the inner surface of the main body 1 with bonding agents 143 and 144.

In each of the above-described embodiments of the present invention, the main body is composed of a top sheet, a back, sheet, and an absorbent member which are different cover stock materials. However, the present invention can be advantageously applied to two-part main body structure in which the front waist portion is composed of a top sheet, a back sheet, and an absorbent member and the rear portion is composed of a top sheet, a back sheet, and an absorbent member connected at the crotch portion. In particular, when the manufacturing process shown in FIGS. 15 and 16 is used, the step for connecting the front portion and the rear portion and the step for applying the elastic leakage protective member can be performed at the same time to improve manufacturing efficiency.

Figure 21:
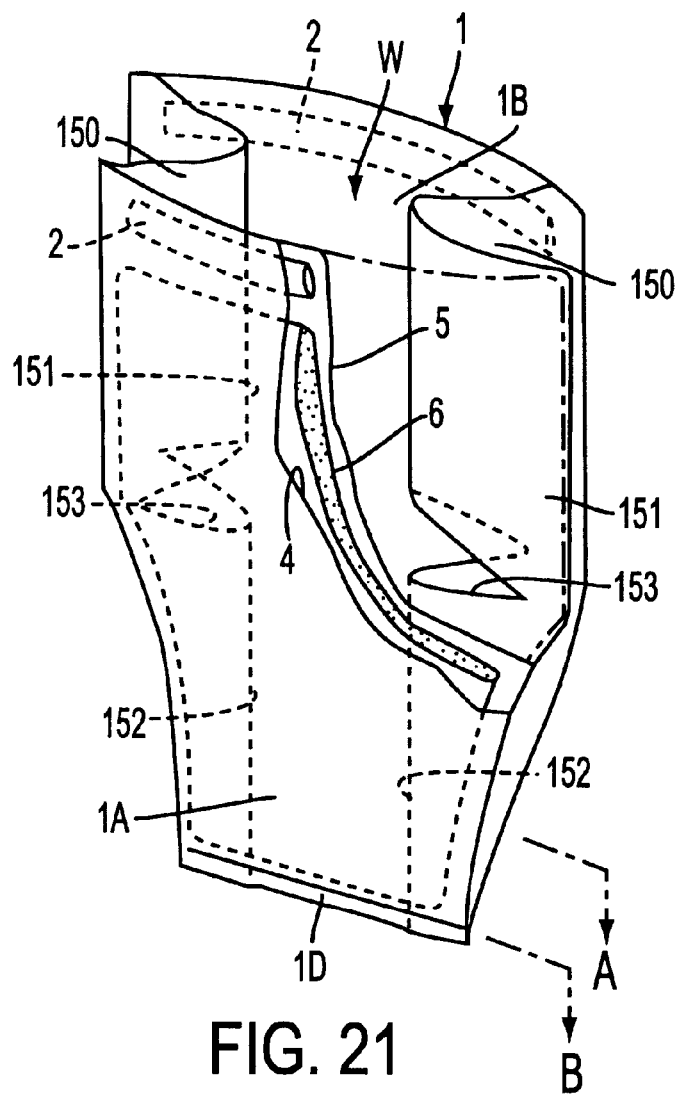
FIG. 21 is a partial exploded view showing an absorbent article according to another preferred embodiment.

FIG. 21 shows a tape-less diaper type absorbent article according to an eighth preferred embodiment. A main body 1 of the absorbent article shown in FIG. 21 is composed of a front waist portion 1A, a rear waist portion 1B and a pair of elastic leakage protective members 150 which fiction as side panels which connect both sides of the front waist portion 1A, the rear waist portion 1B, and both the leakage protective members 150 are mutually connected by a connection portion 1D. Thus, the absorbent article shown in FIG. 21 is formed in a cylindrical shape of which one end thereof is closed. The upper open end forms waist hole W.

The front portion 1A is composed of a liquid permeable top sheet 5, a liquid impermeable back sheet 4, and an absorbent member 6 disposed therebetween. The structure of the rear portion 1B is similar to that of the front portion 1A. Elastic waist gathers 2 are optionally disposed at the front waist portion 1A and the rear waist portion 1B along the waist hole W.

Each of the leakage protective members 150 is formed from a sheet material which has a suitable elasticity at least in the lateral direction. The leakage protective member 150 is formed in a nearly rectangular shape. Before the absorbent article is used, each of the leakage protective members 150 is folded along its length. Each of the leakage protective members 150 have openings 153 at a central longitudinal position. The opening 153 sections the leakage protective member 150 between an upper zone 151 and a lower zone 152.

Figure 22A:
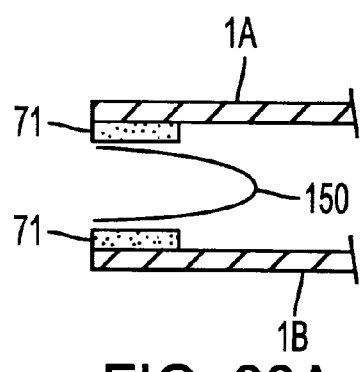
FIG. 22A is a partial sectional view taken along line A shown in FIG. 21.
Figure 22B:
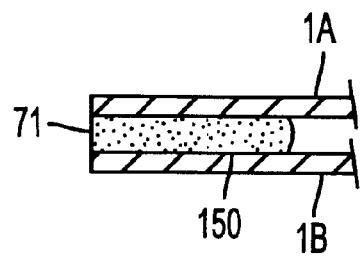
FIG. 22B is a partial sectional view taken along line B shown in FIG. 21.

As shown in FIG. 22B, the lower edge of each leakage protective members 150 is folded and integrally connected to the lower edge of the front portion 1A and the rear portion 1B at 1D with a suitable bonding agent 71 such as a hot-melt bonding agent. As shown in FIG. 22A, above connection portion 1D, the side edges of each of the leakage protective members 150 are connected to the side edges of the front and rear waist portions 1A, 1B, respectively, with bonding agent 71. Thus, the folded elastic leakage protective members 150 do not widen at the connection portion 1D, but freely spread out above connection portion 1D.

Figure 23:
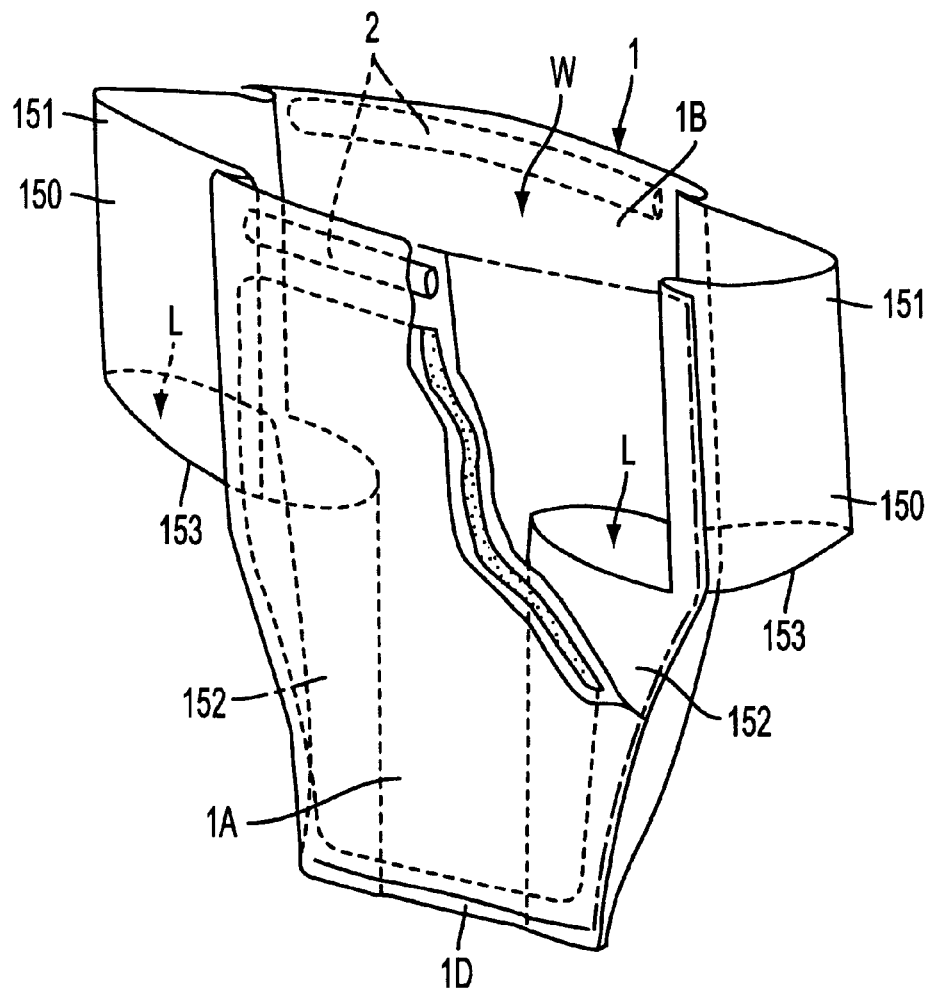
FIG. 23 is a partial exploded view showing the upper zone of an elastic leakage protective member of the absorbent article shown in FIG. 21 expanded before installation.

When applying the absorbent article shown in FIG. 21, upper zones 151 are spread out from both side edges of the front and rear waist portions 1A, 1B as shown in FIG. 23. Upper zones 151 thus form a cylindrical shape. The openings 153 of the elastic leakage protective members 150 form leg holes L.

Figure 24:
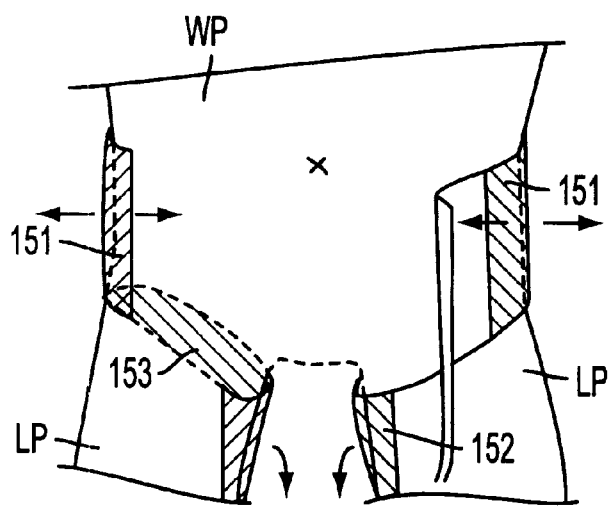
FIG. 24 is a schematic diagram of the absorbent article shown in FIG. 21 when worn.
Figure 25:
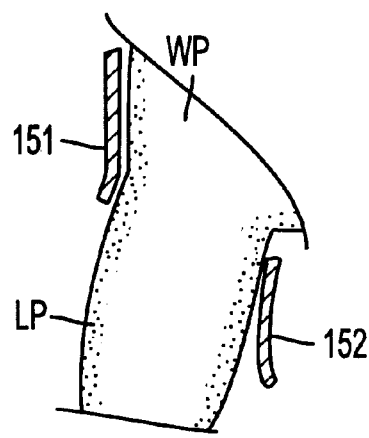
FIG. 25 is a schematic diagram of the absorbent article shown in FIG. 21 when worn.

FIGS. 24 and 25 show the elastic leakage protective members 150 of FIG. 23 contacting the body in use. The upper zones 151 of the elastic leakage protective members 150 are positioned on both sides of the waist portion of the wearer. The lower zones 152 are positioned inside the femoral portions.

The upper zones 151 securely holds the absorbent article at a predetermined position, but the absorbent article does not inhibit the movement of the wearer. The lower zones 152 snuggly fit the inside of the femoral base portions of the wearer, provide an excellent leakage protective effect especially required for these portions, and prevent body exudate from leaking up to their absorbing limits.

As an important feature of the absorbent article, the elastic leakage protective members 150 are sectioned along upper zones 151, lower zones 152, and openings 153. Since the upper zones 151 are vertically less restricted, after the wearer spreads out the absorbent article and wears it, the upper zones 151 expand and shrink in response to the motions of the waist portion of the wearer. On the other hand, since the lower zones 152 are connected to the front and rear crotch portion, they restrict the outward motions of the wearer, thereby maintaining a stable standing cuff state. Thus, since both the upper zones 151 and the lower zones 152 expand and shrink in opposite directions, their retractive forces do not interfere with one another. Consequently, the absorbent article provides an improved leakage protective effect.

Figure 26:
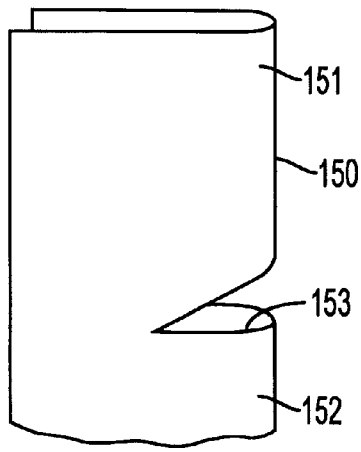
FIG. 26 is a perspective view showing a portion of the elastic leakage protective member of FIG. 21.
Figure 27:
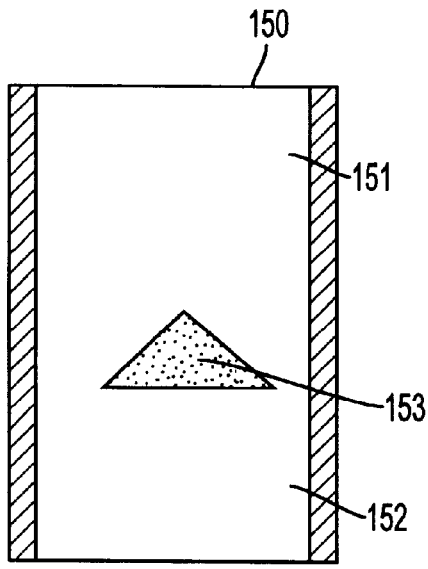
FIG. 27 is a plan view of part of the elastic leakage protective member of FIG. 21.
Figure 28:
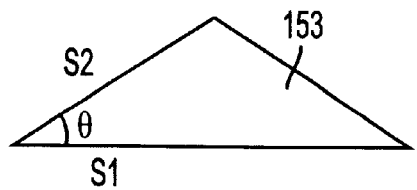
FIG. 28 is a schematic diagram approximating the area of the opening formed in an elastic leakage protective member.

In the embodiment shown in FIGS. 21 to 25, when the absorbent article is folded, the openings 153 in the elastic leakage protective members 150 are formed in a wedge shape as shown in FIG. 26. When the absorbent article is spread out, the openings 153 in the elastic leakage protective members 150 approximate isosceles triangles where the height is relatively small compared with the base as shown in FIG. 27. Assuming that the length of the base S1 of the isosceles triangle is constant, the area of the opening 153 is proportional to the angle θ of the base S1 and the hypotenuse S2. Thus, by varying the angle θ, the size of the opening 153 can be changed.

Figure 29:
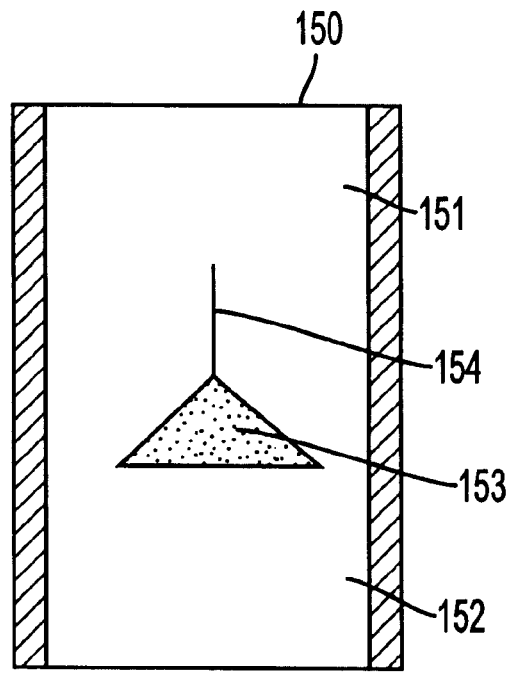
FIG. 29 is a plan view of another embodiment of an elastic leakage protective member.

In addition, as shown in FIG. 29, a score line 154 may optionally be formed upwardly from the apex of the isosceles triangle in the upper zone 151. The score line 154 may be a fine perforation which does not pass liquid. Score line 154 facilitates removal of elastic leakage protective member 150. However, when the strength necessary for tearing the elastic sheet material of the leakage protective member 150 is not too large, it can be torn without the auxiliary score line 154.

Figure 30:
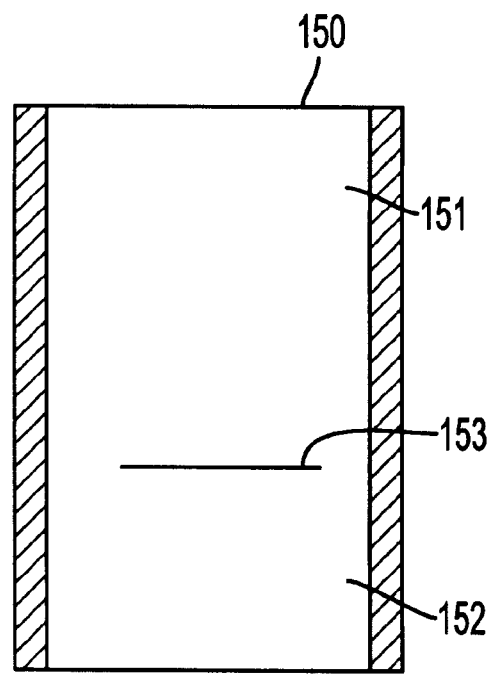
FIG. 30 is a plan view of another embodiment of an elastic leakage protective member.

As shown in FIG. 30, the opening 153 may alternatively be a slit 153.

As another advantage of the absorbent article shown in FIGS. 21 to 30, since the leakage protective members 150 have been folded inside the front waist portion 1A and the rear waist portion 1B, a folding step is not required unlike conventional manufacturing methods. Thus, the packaging of the products can be simplified and easily performed. In addition, the value of a packaged product decreases, so the products may be easily stored and transported.

The material of the elastic leakage protective members 150 may be the same as the material used in the embodiment shown in FIGS. 1 and 2.

Figure 31:
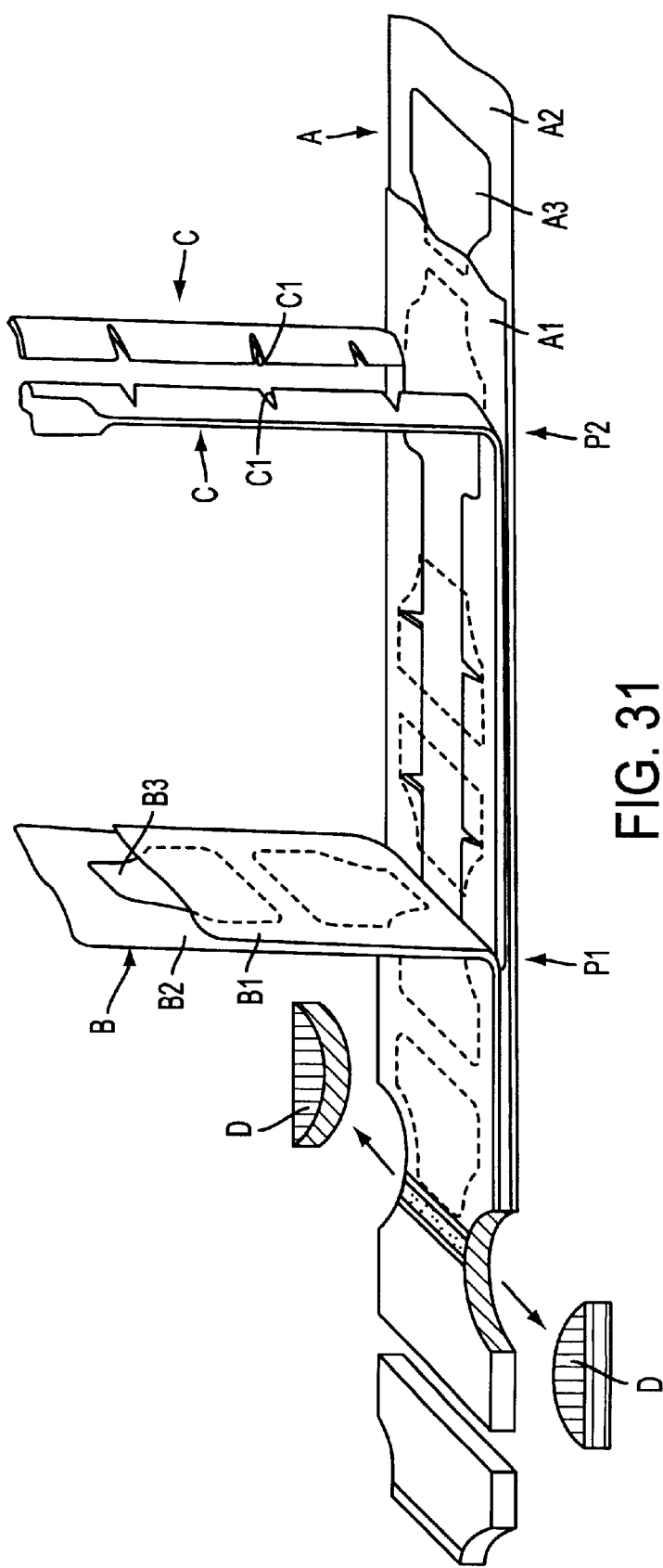
FIG. 31 is a schematic diagram of a manufacturing process for making an absorbent article according to another preferred embodiment.

FIG. 31 shows the principal manufacturing steps of the absorbent article according to the preceding embodiment. In FIG. 31, A represents a first assembly which eventually becomes the front waist portion of the absorbent garment. B represents a second assembly which eventually becomes the rear waist portion of the garment. The first assembly layers top sheet A1, absorbent articles A3, and back sheet A2. The absorbent articles A3 are disposed between the top sheet A1 and the back sheet A2 at predetermined intervals. The first assembly A is conveyed at a predetermined speed in the longitudinal direction. Likewise, the second assembly B layers top sheet B1, absorbent articles B3, and back sheet B2. The absorbent articles B3 are disposed between the top sheet B1 and the back sheet B2 at predetermined intervals. The second assembly B is conveyed in the longitudinal direction in synchronization with the first assembly A.

The first assembly A and the second assembly B are layered by, e.g., a guide roller so that each absorbent article A3 faces each absorbent article B3 at a position P1 of the conveying path.

On the other hand, at a position P2, a pair of sheet members C which become elastic leakage protective members are continuously supplied on the top sheet A1 of the first assembly A. Each of the sheet members C is formed by folding a web member along the width thereof. In this embodiment, V-shaped openings (openings C1 in the spread state) are formed from the folded edge to the opposite edge. The sheet members C are supplied to both edges of the first assembly so that the folded edges face each other. A hot-melt type bonding agent supplied from a nozzle (not shown) is applied to predetermined positions of members C.

When the first assembly A and the sheet members C reach position P1, the second assembly B is layered on the sheet members C. The resultant layered members are supplied to a heat-bonding unit (not shown) which bonds the layered members with a hot-melt type bonding agent. Finally, leg openings D are cut out and each absorbent article is separated from the layered members.

The above-described method is generally referred to as a longitudinal manufacturing method. In this method, each material is conveyed in parallel with the side edges of products. However, the present invention can be also applied for lateral manufacturing methods.

Figure 32:
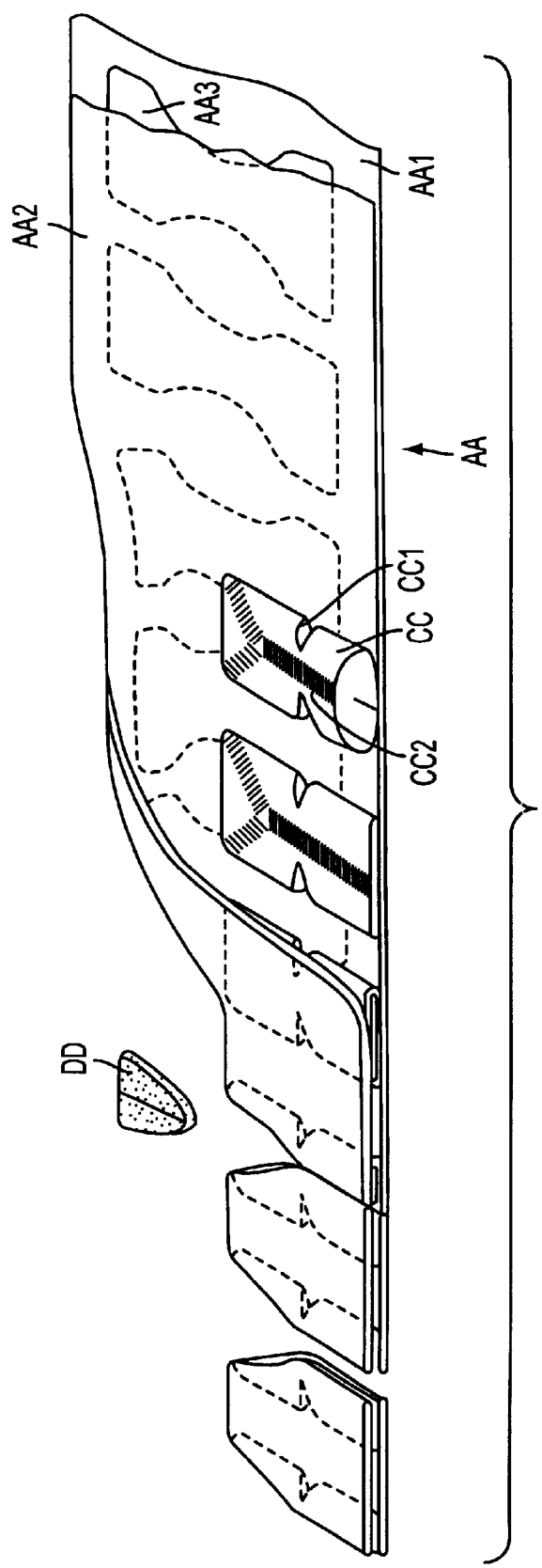
FIG. 32 is a schematic diagram of a manufacturing process for making an absorbent article according to another preferred embodiment.

In the lateral manufacturing method, as shown in FIG. 32, a back sheet AA1 and a top sheet AA2 are layered. Absorbent members AA3 are placed between the back sheet AA1 and the top sheet AA2 at predetermined intervals. Thus, a first assembly AA is formed. While the first assembly AA is being conveyed in the longitudinal direction at a predetermined speed, a second assembly CC places leakage protective members between absorbent members AA3. Assembly CC has slits CC1 at predetermined positions. A bonding agent CC2 such as a hot-melt type bonding agent is applied to predetermined positions of the assembly CC.

After the second assembly CC is positioned, the first assembly is folded in half. Thus, the second assembly CC is sandwiched with the first assembly AA. After the first assembly AA and the second assembly CC are bonded at predetermined positions, leg holes are cut by removing portion DD.

In any of the above-described manufacturing methods, the folding step for folding the products in half can be omitted. The volume of the products thus becomes small. Consequently, the products can be easily packaged and handled.

As described above, a pair of elastic leakage protective members are attached to the main body in such a manner that the elastic leakage protective members cover at least part of the respective leg holes. The leakage protective members improve the fit and leakage protective effect over prior art designs.

In addition, the absorbent articles can be effectively mass-produced by the methods of the present invention. Thus, the quality of the products can be assured and the cost thereof can be reduced.

The pair of elastic leakage protective members, each of which is formed from a first portion which closes part of a leg hole and a second portion which connects one or both edges of the first portion to the top sheet, allow the legs of a wearer to extend therethrough in the leg holes and the body of the wearer to fit in the crotch portion, thereby improving the fit, feel and leakage protective effect.

When both side edges of a front waist portion and a rear waist portion of an absorbent article are connected with a pair of elastic leakage protective members each of which is internally folded in half and the leakage protective members have openings as leg holes, each of the elastic leakage protective members is sectioned between an upper zone above the opening and a lower zone below the opening. In use, the upper zone expands along the waist portion of the wearer. The lower zone maintains contact with the inside of the femoral base portions of the wearer.

While the invention has been described in connection with the preferred embodiments, it is not limited thereto. It will be readily understood by those of ordinary skill in the art that modifications may be made to the preferred embodiments without departing from the scope of the invention as defined by the appended claims.

What is claimed is:

1. An absorbent article for fitting around a wearer's waist and legs, comprising:
   a top sheet;
   a back sheet;
   an absorbent core disposed between said top sheet and said back sheet;
   a main body comprising a discrete front waist portion having a top edge and a bottom edge and a discrete rear waist portion having a top edge and a bottom edge;
   wherein said front waist portion is attached to said rear waist portion along the bottom edges thereof to form a crotch portion;
   wherein said front waist portion, said rear waist portion and said crotch portion have side edge portions;
   a pair of leakage protective members disposed on said main body interconnecting said front waist portion and said rear waist portion, said leakage protective members attached to respective side edge portions of the front waist portion, the rear waist portion and the crotch portion over substantially the entire length of said front waist portion, rear waist portion and crotch portion to form an annularly continuous waist opening;
   each leakage protective member comprising an elastic composite sheet material and an upper zone and a lower zone defined by an opening formed at a predetermined position between upper and lower edges thereof;
   whereby the opening of each leakage protective member provides a leg hole opening such that the upper zone is contactable with the wearer's waist and the lower zone is contactable with an inner side of the wearer's leg.

2. The absorbent article according to claim 1, wherein the leg hole opening approximates an ellipse.

3. The absorbent article according to claim 1, further comprising a slit formed in each of said elastic leakage protective members.

4. The absorbent article according to claim 1, further comprising a cross-shaped slit formed in each of said elastic leakage protective members.

5. The absorbent article according to claim 1, further comprising a Y-shaped slit formed in each of said elastic leakage protective members.

6. The absorbent article according to claim 1, further comprising a slit formed in each of said elastic leakage protective members, and closure members mounted to the leakage protective members, respectively, for closing the absorbent article.

7. The absorbent article according to claim 1 wherein each leakage protective member comprises a seamless sheet material having a unitary structure.

8. The absorbent article according to claim 1 wherein said opening comprises a horizontal slit formed along each leakage protective member.

9. The absorbent article according to claim 1 wherein said opening in each leakage protective member approximates the shape of an equilateral triangle.

10. The absorbent article according to claim 9, further comprising a slit extending from the apex of the triangle.

11. A method of manufacturing an absorbent article having a main body comprising a front waist portion, a rear waist portion and a crotch portion, comprising the steps of:
    conveying a first continuous web assembly along a conveying path, said first continuous web assembly comprising a top sheet, a back sheet and a series of absorbent cores disposed therebetween, said first continuous web assembly having lateral side edges, wherein said first continuous web assembly forms said front waist portion of said absorbent article;
    supplying continuously to respective lateral side edges of the first assembly a pair of elastic sheet materials at a first position on the conveying path, each of said elastic sheet materials folded in half to form overlapping lateral side edges and having openings at predetermined intervals adjacent said absorbent cores, respectively, corresponding to respective leg openings;
    superimposing a second continuous web assembly onto the first continuous web assembly and elastic sheet materials at a second position on the conveying path, said second continuous web assembly comprising a top sheet, a back sheet and a series of absorbent cores disposed therebetween, said second continuous web assembly having lateral side edges wherein said second continuous web assembly forms said rear waist portion of said absorbent article;
    joining the first assembly, the second assembly and the elastic sheet materials along said lateral side edges thereof and along portions thereof corresponding to respective crotch portions to form a single, integrated web assembly; and
    cutting the integrated web assembly at a third position on the conveying path to obtain said absorbent article.

12. The method according to claim 11 wherein the step of joining is carried out by means of a hot melt adhesive agent applied at a predetermined position.

13. A method of manufacturing an absorbent article having a main body comprising a front waist portion, a rear waist portion and a crotch portion comprising the steps of:

provided pairs of elastic sheet members having top edges, bottom edges and side edges;

superimposing said elastic sheet members of each pair on one another;

bonding said pairs of superimposed elastic sheet members at side edge portions thereof;

opening said bonded sheet members so as to form cylindrical subassemblies by spreading each elastic sheet member outwardly at its central portion until the bonded side edge portions of each pair of bonded elastic sheet members are approximately adjacent each other to thereby form elastic leakage protective member subassemblies each having a top edge, a bottom edge, a front face and a rear face;

wherein said pairs of elastic sheet members are configured such that one opening having a peripheral edge is present in each of the front and rear faces of said elastic leakage protective member subassembly;

preparing a first assembly comprising a continuous top sheet, a continuous back sheet and absorbent members disposed therebetween at predetermined intervals, said first assembly having lateral side edges wherein the first assembly forms the front portion of the absorbent article;

preparing a second assembly comprising a continuous top sheet, a continuous back sheet and absorbent members disposed therebetween at predetermined intervals, said second assembly having lateral side edges wherein the second assembly forms the rear portion of the absorbent article;

continuously supplying the first assembly and the second assembly to a predetermined intersecting point at a speed synchronized to superimpose respective absorbent members of said first and second assemblies;

supplying said elastic leakage protective member subassemblies to one of the first and second assemblies to superimpose said absorbent members, respectively, before the intersecting point;

bonding the first and second assemblies and the elastic leakage protective member subassemblies at predetermined bonding regions along the lateral side edges thereof and along portions thereof corresponding to respective crotch portions; and cutting the superimposed, bonded first and second assemblies along a predetermined line to form said absorbent article.

14. The method according to claim 13 further comprising the step of applying hot melt adhesive agent to the peripheral edge of the one of said openings of each elastic leakage protective member subassembly and the bottom edge of each elastic leakage protective members subassembly.

15. The method according to claim 13, wherein said step of superimposing two elastic sheet members of each pair on one another comprises the step of superimposing two substantially similar I-shaped sheet members each having an opening at both side edge portions thereof; and said bonding step comprises the step of bonding the I-shaped sheet members of each pair along said side edge portions to form a cylindrical member.

16. A method of manufacturing an absorbent article having front and rear waist portions and a crotch portion therebetween, said front and rear waist portions and said crotch portion having side edge portions defining a periphery of the absorbent article, a pair of leakage protective members made of an elastic sheet material interconnecting the front and rear waist portions by attaching the respective side edge portions of the front waist portion, rear waist portion and crotch portion over the entire length thereof to form an annularly continuous waist opening, each leakage protective member divided into the upper zone and the lower zone by an opening formed at a predetermined position between an upper and lower edge thereof, comprising:

superimposing a top sheet, a back sheet, and absorbent members therebetween at predetermined intervals to form a first assembly which forms the front waist portion;

superimposing a top sheet, a back sheet and absorbent members therebetween at predetermined intervals to form a second assembly which forms the rear waist portion;

continuously supplying the first and second assemblies at a predetermined intersecting point P1 on a conveying path at a speed synchronized so that respective absorbent members face each other;

folding a pair of continuous elastic sheet materials, which form the leakage protective members, in half to form a pair of subassemblies;

forming an opening in each of the leakage protective members at predetermined locations;

continuously supplying the subassemblies to one of the first and second assemblies along the side edge portions thereof, respectively, with said opening adjacent said absorbent members, respectively, at a point P2 prior to point P1 on the conveying path;

bonding the first and second assemblies and the leakage protective members at predetermined bonding portions; and cutting the bonded first and second assemblies along a predetermined line to form said absorbent article.

17. A method of manufacturing an absorbent article having front and rear waist portions and a crotch portion therebetween, said front and rear waist portions and said crotch portion having side edge portions defining a periphery of the absorbent article, a pair of leakage protective members made of an elastic sheet material interconnecting the front and rear portions by attaching respective side edge portions of the front waist portion, the rear waist portion and the crotch portion over the entire length thereof to form an annularly continuous waist opening, each leakage protective member divided into an upper zone and a lower zone by an opening formed at a predetermined position between an upper edge and a lower edge, comprising:

superimposing continuous strip-like top sheet and back sheet web materials with absorbent members sandwiched therebetween at predetermined intervals to form a first assembly;

forming second assemblies made of an elastic sheet material, each of which takes the form of a cylinder of predetermined length and having a slit formed at both side edge portions of the cylinder;

supplying the second assemblies onto the first assembly at said predetermined intervals;

folding the first assembly in half to sandwich the second assemblies therebetween;

bonding the first and second assemblies at predetermined bonding regions; and cutting the bonded first and second assemblies along a predetermined line to form said absorbent article.

* * * * *